(12) United States Patent
Hoefer et al.

(10) Patent No.: US 9,211,149 B2
(45) Date of Patent: Dec. 15, 2015

(54) SURGICAL APPARATUS

(71) Applicant: Aesculap AG, Tuttlingen (DE)

(72) Inventors: Fabian Hoefer, Tuttlingen (DE); Dirk Ley, Rückersdorf (DE); Volker Maute, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 251 days.

(21) Appl. No.: 13/955,166

(22) Filed: Jul. 31, 2013

(65) Prior Publication Data

US 2014/0039567 A1  Feb. 6, 2014

(30) Foreign Application Priority Data

Aug. 1, 2012  (DE) .......................... 10 2012 107 056

(51) Int. Cl.
*A61B 17/88*  (2006.01)
*A61B 17/70*  (2006.01)
*A61B 19/00*  (2006.01)

(52) U.S. Cl.
CPC ........... *A61B 17/7083* (2013.01); *A61B 17/708* (2013.01); *A61B 17/7082* (2013.01); *A61B 17/7032* (2013.01); *A61B 17/7091* (2013.01); *A61B 2019/461* (2013.01)

(58) Field of Classification Search
CPC ............. A61B 17/7083; A61B 17/708; A61B 17/7082; A61B 17/7032; A61B 17/7091; A61B 2019/461

USPC ........... 606/86 A, 105, 99, 90, 246, 264, 265, 606/270

See application file for complete search history.

(56) References Cited

U.S. PATENT DOCUMENTS

| 7,922,731 | B2 | 4/2011 | Schumacher et al. | |
|---|---|---|---|---|
| 7,998,144 | B2 | 8/2011 | Schumacher et al. | |
| 8,043,343 | B2 | 10/2011 | Miller et al. | |
| 2005/0154389 | A1* | 7/2005 | Selover et al. | 606/61 |
| 2005/0245928 | A1* | 11/2005 | Colleran et al. | 606/61 |
| 2007/0173831 | A1* | 7/2007 | Abdou | 606/61 |
| 2008/0125788 | A1 | 5/2008 | Cohen et al. | |

* cited by examiner

*Primary Examiner* — Pedro Philogene
*Assistant Examiner* — David C Comstock
(74) *Attorney, Agent, or Firm* — RatnerPrestia

(57) ABSTRACT

The present invention relates to a surgical apparatus for the implantation of a spinal column stabilization system generally, and more specifically to a surgical apparatus for the implantation of a spinal column stabilization system, which spinal column stabilization system comprises at least two bone screws which are respectively anchorable in a vertebra of a spinal column and which respectively comprise at least one first connecting element seating, and at least one connecting element which corresponds to the first connecting element seating and is insertable and fixable therein, wherein the apparatus comprises at least one multi-function sleeve having a proximal and a distal end, which multi-function sleeve defines a longitudinal axis and comprises a connecting element coupling device, a spreading-device coupling device and a holding instrument coupling device.

25 Claims, 24 Drawing Sheets

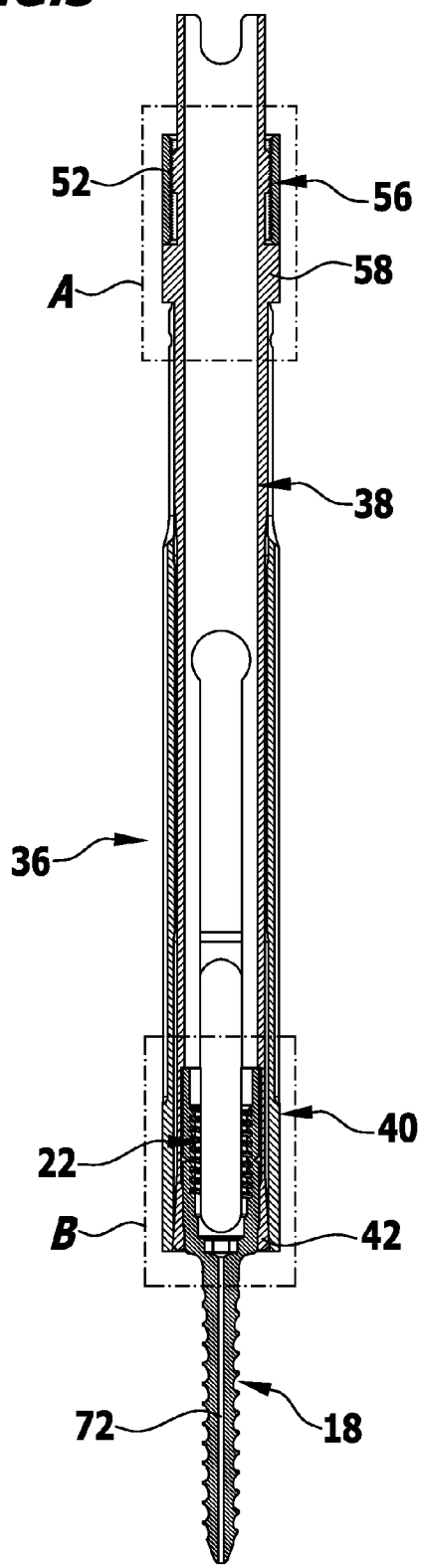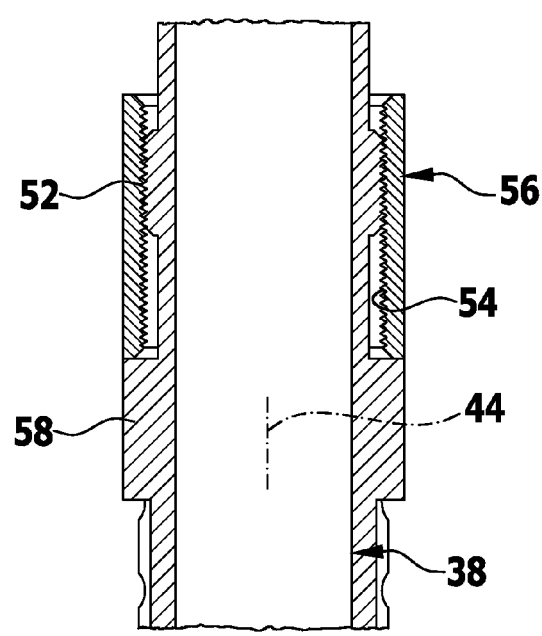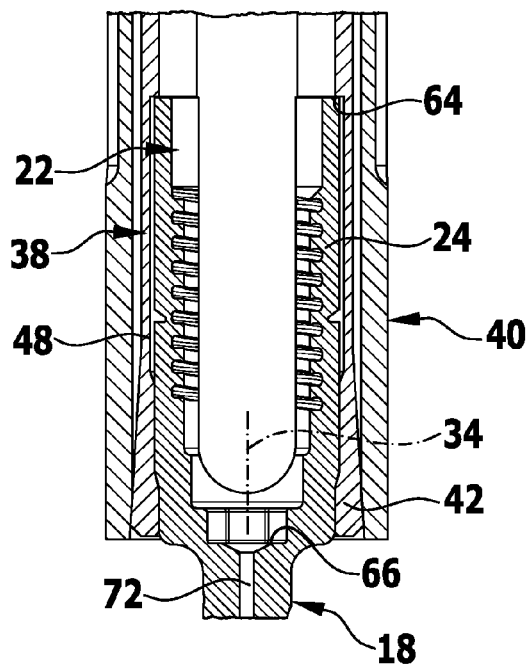

SURGICAL APPARATUS

CROSS-REFERENCE TO RELATED APPLICATIONS

Figure 1:
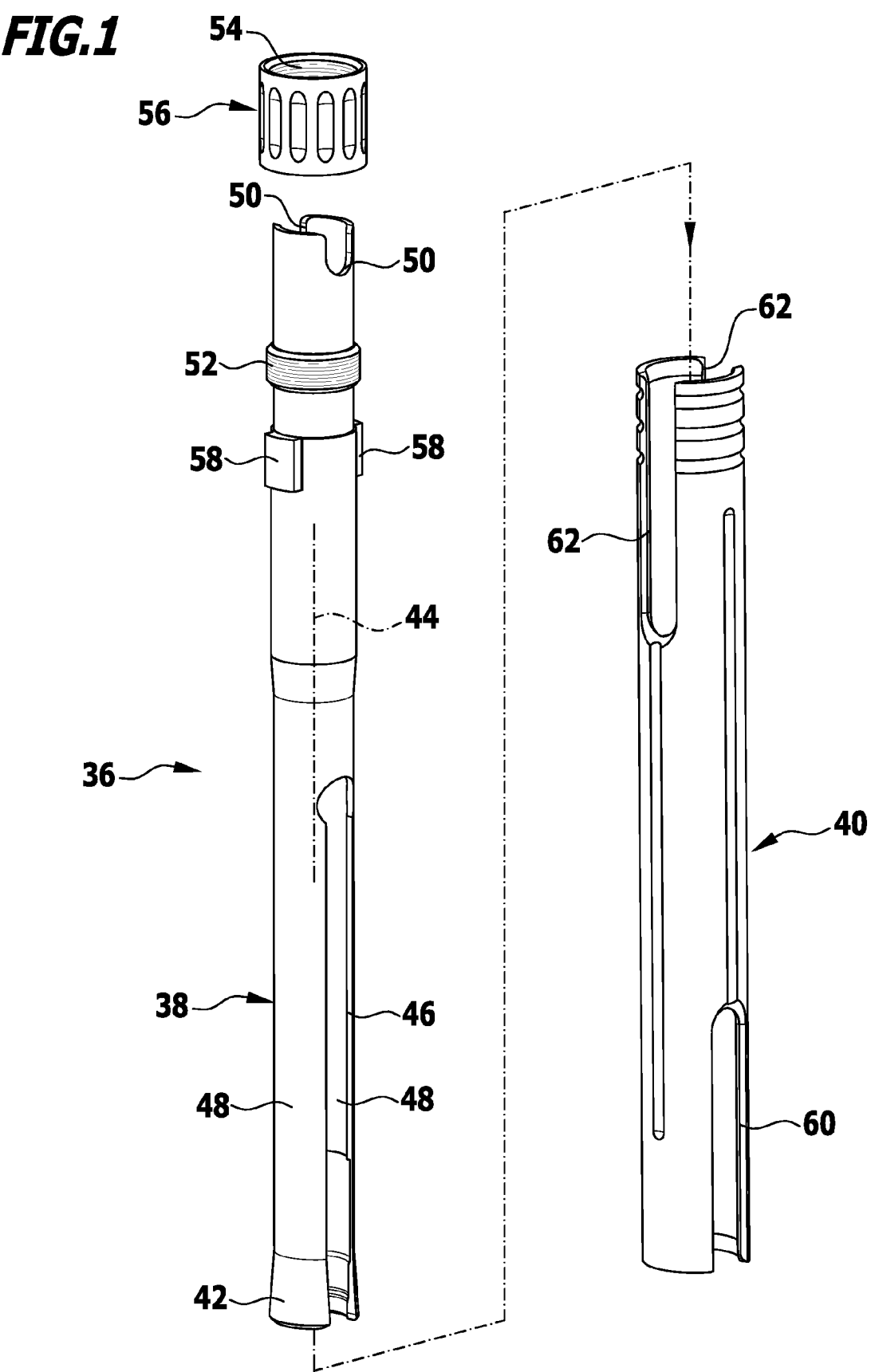

This application claims priority to German patent application number 10 2012 107 056.3, filed Aug. 1, 2012, which is incorporated by reference herein in its entirety and for all purposes.

FIELD OF THE INVENTION

The present invention relates to surgical apparatus for the implantation of a spinal column stabilization system generally, and more specifically to a surgical apparatus for the implantation of a spinal column stabilization system, which spinal column stabilization system comprises at least two bone screws which are respectively anchorable in a vertebra of a spinal column and which respectively comprise at least one first connecting element seating, and at least one connecting element which corresponds to the first connecting element seating and is insertable and fixable therein, wherein the apparatus comprises at least one multi-function sleeve having a proximal and a distal end, which multi-function sleeve defines a longitudinal axis and comprises a connecting element coupling device, a spreading-device coupling device and a holding instrument coupling device.

BACKGROUND OF THE INVENTION

An apparatus of the type described hereinabove is known from U.S. Pat. No. 7,922,731 B2 for example. It is employed, in particular, in the course of a surgical procedure in order to fix a spinal column stabilization system as described above to a spinal column. The implantation of such spinal column stabilization systems originally began using open techniques. This means that an operating surgeon has a free view of the site of the operation. However, in order to minimise operational traumata for the patients, the operational techniques that were also known for the implantation of spinal column stabilization systems have been further developed with the goal of also implanting such spinal column stabilization systems in a minimally invasive manner.

In the case of the apparatus known from U.S. Pat. No. 7,922,731 B2, the bone screws of the spinal column stabilization system are each initially placed in a vertebra. The multi-function sleeve of this spinal column stabilization system is then seated on the forklike head which accommodates the rod-shaped connecting element. The known multi-functional sleeve incorporates guidance members in order to establish a firm grip on the forklike head of the screw. However, it is difficult to seat such a multi-function sleeve on the screw when there is only one minimally invasive access to the vertebra.

Therefore, it would be desirable to provide a surgical apparatus of the type described hereinabove which allows a simpler employment thereof in minimally invasive surgical procedures.

SUMMARY OF THE INVENTION

In accordance with the invention a surgical apparatus for the implantation of a spinal column stabilization system is provided. The spinal column stabilization system comprises at least two bone screws which are respectively anchorable in a vertebra of a spinal column and which respectively comprise at least one first connecting element seating, and at least one connecting element which corresponds to the first connecting element seating and is insertable and fixable therein. The apparatus comprises at least one multi-function sleeve having a proximal and a distal end, which multi-function sleeve defines a longitudinal axis and comprises a connecting element coupling device, a spreading-device coupling device and a holding instrument coupling device. The multi-function sleeve comprises an internal wall surface which is rotationally symmetrical with respect to the longitudinal axis, and no projections protrude from the internal wall surface or beyond it in the direction of the longitudinal axis.

BRIEF DESCRIPTION OF THE DRAWING FIGURES

Figure 2:
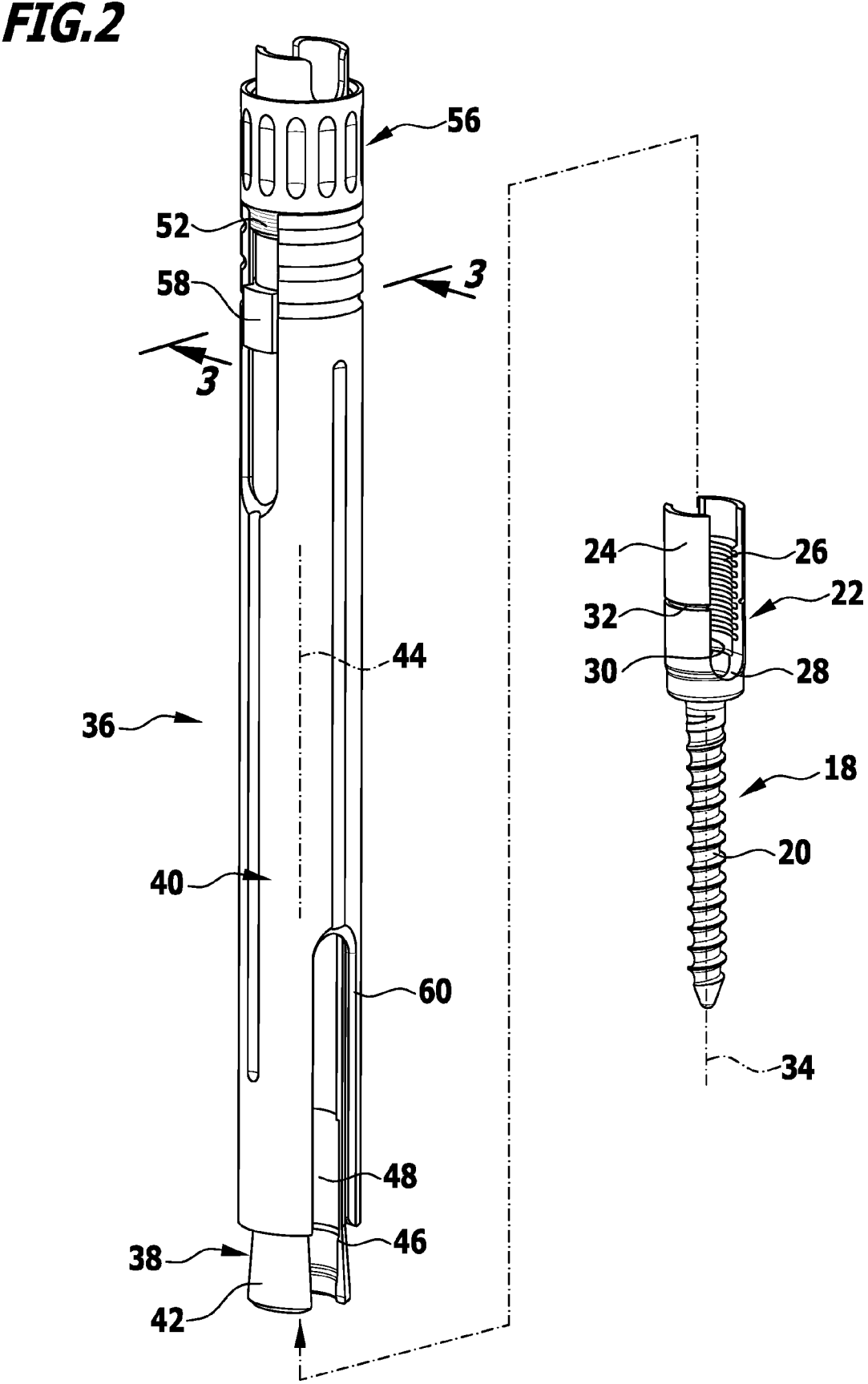
Figure 4:
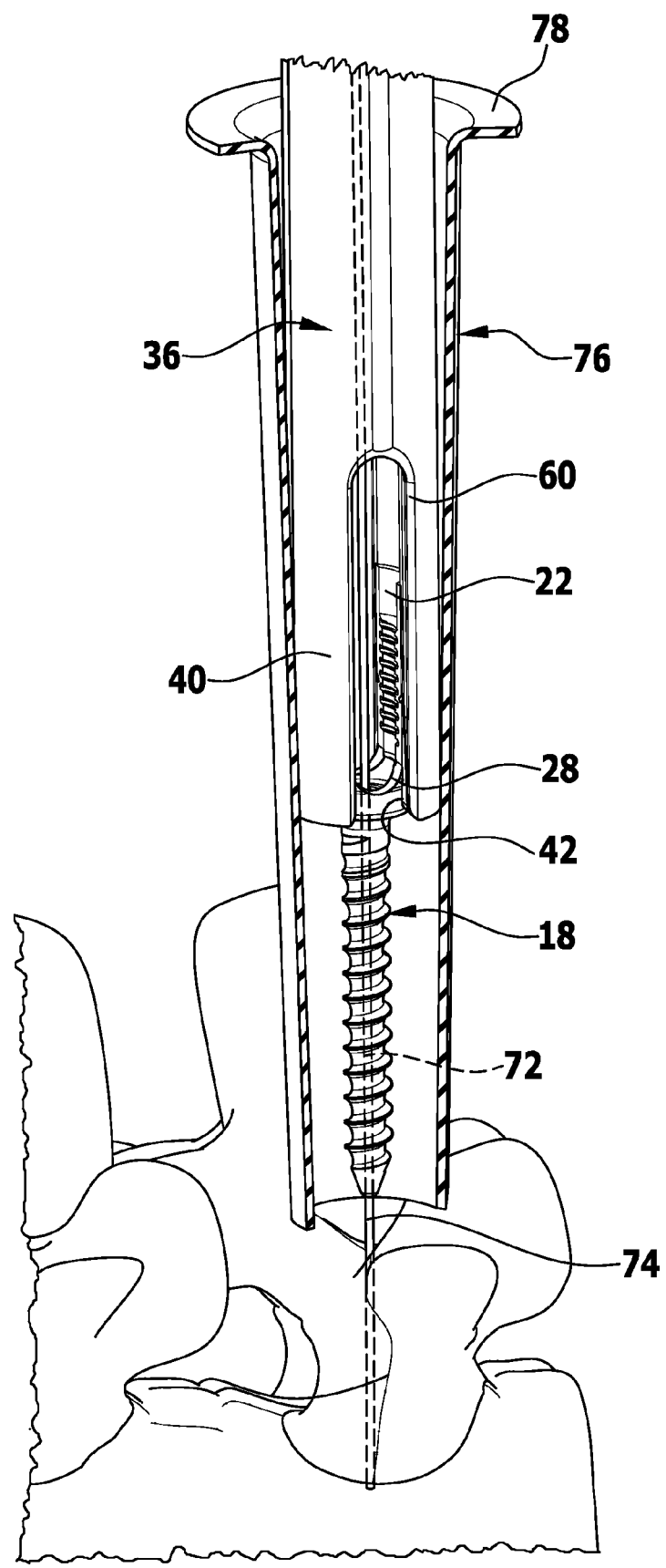
Figure 5:
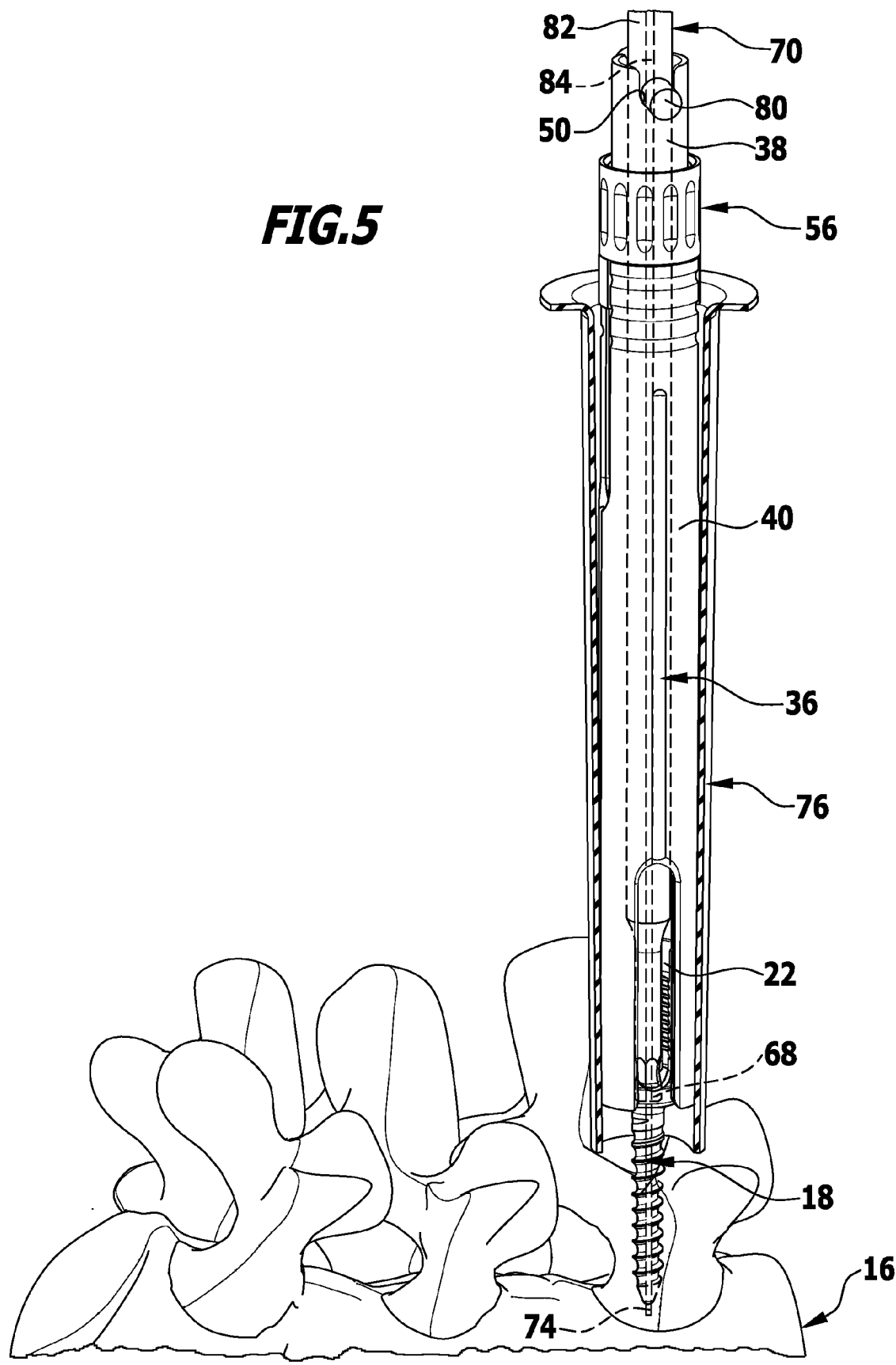
Figure 6:
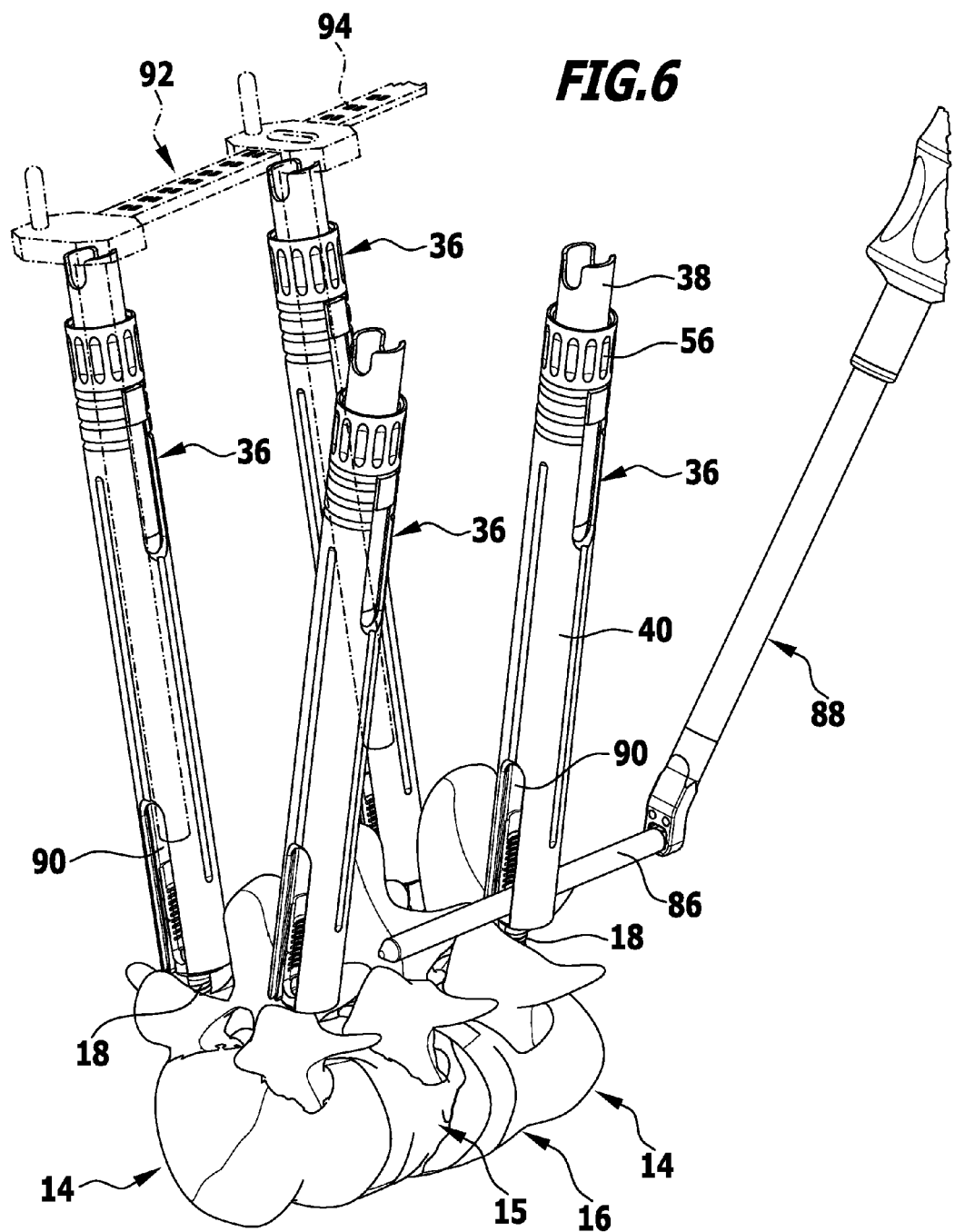
Figure 7:
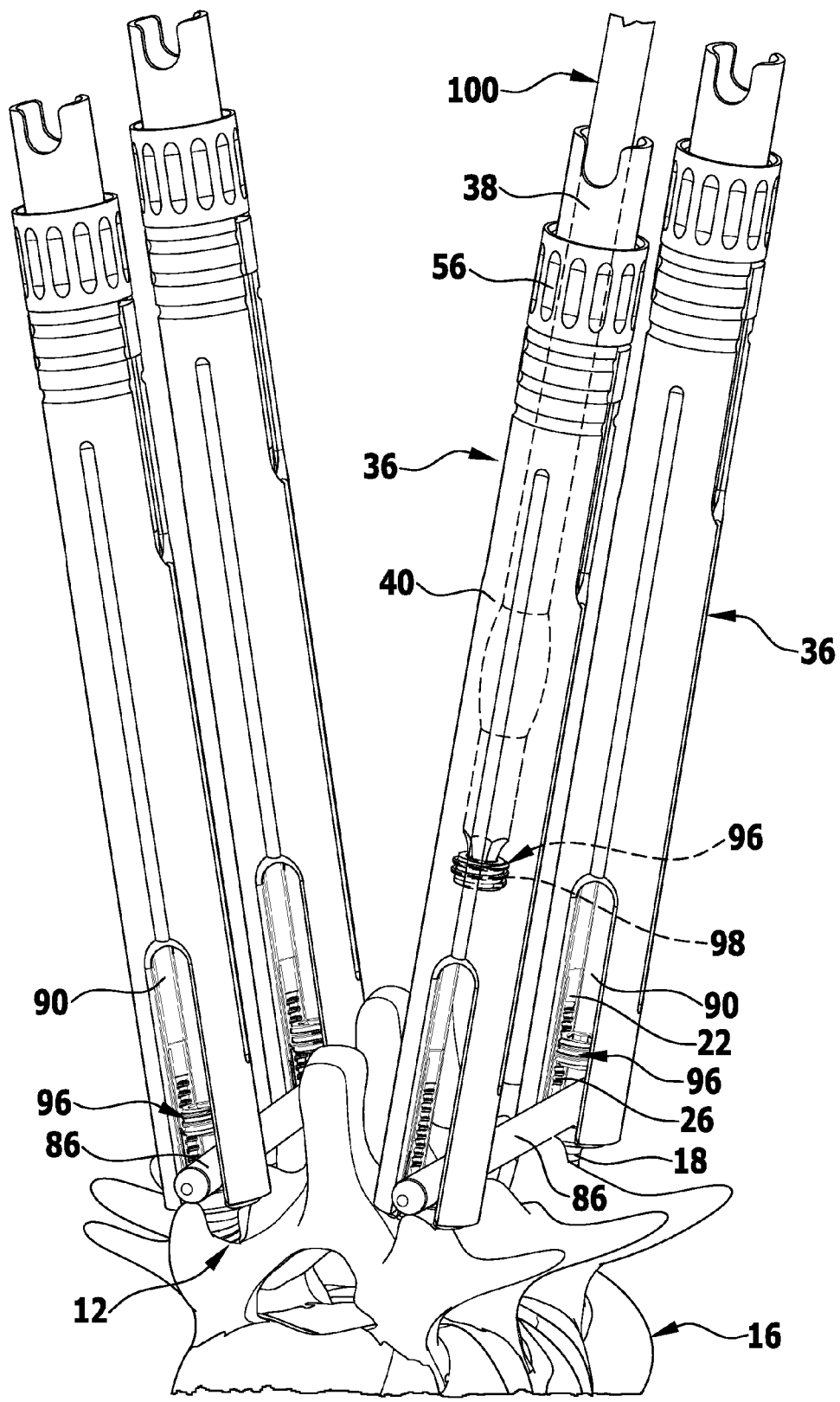
Figure 8:
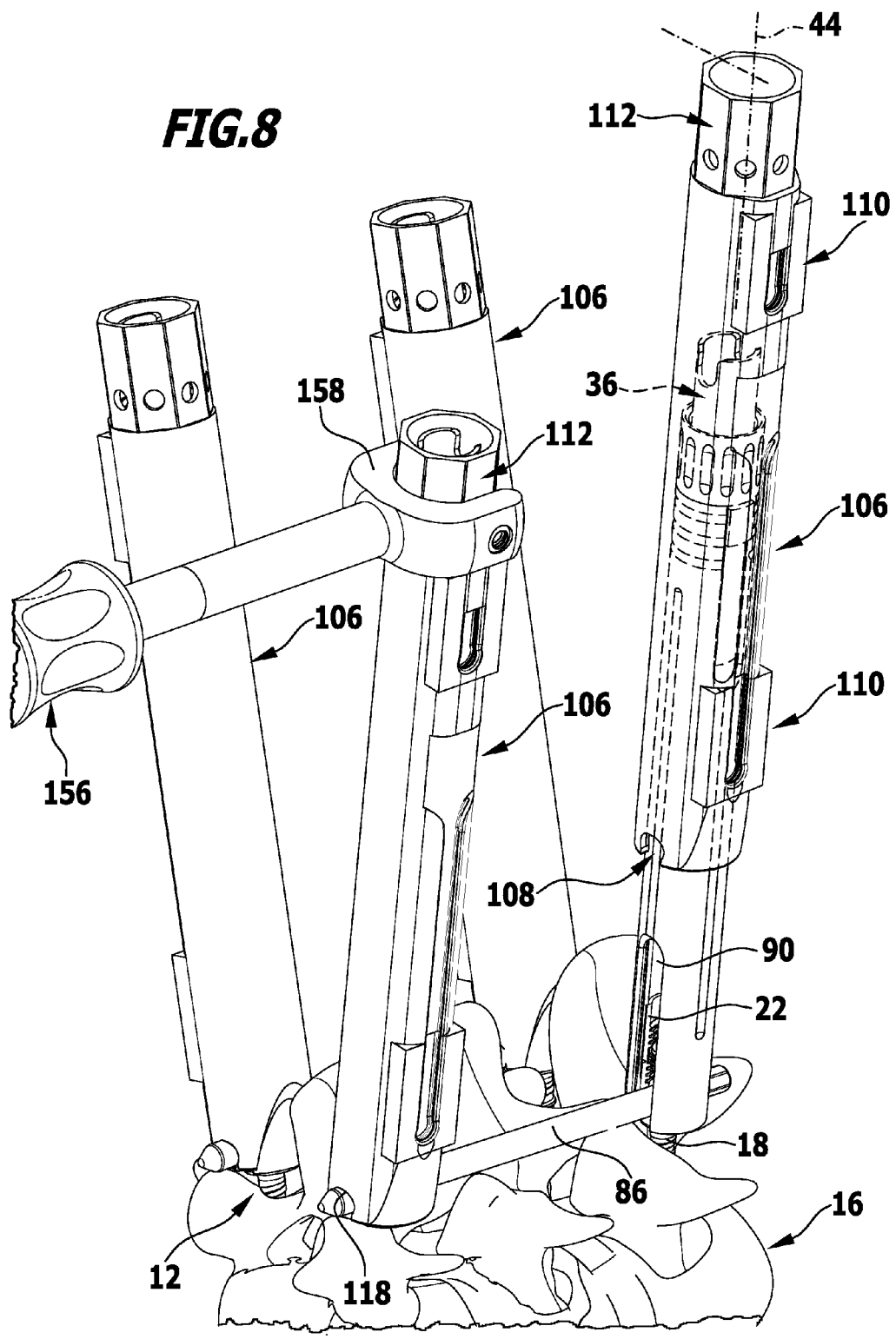
Figure 9:
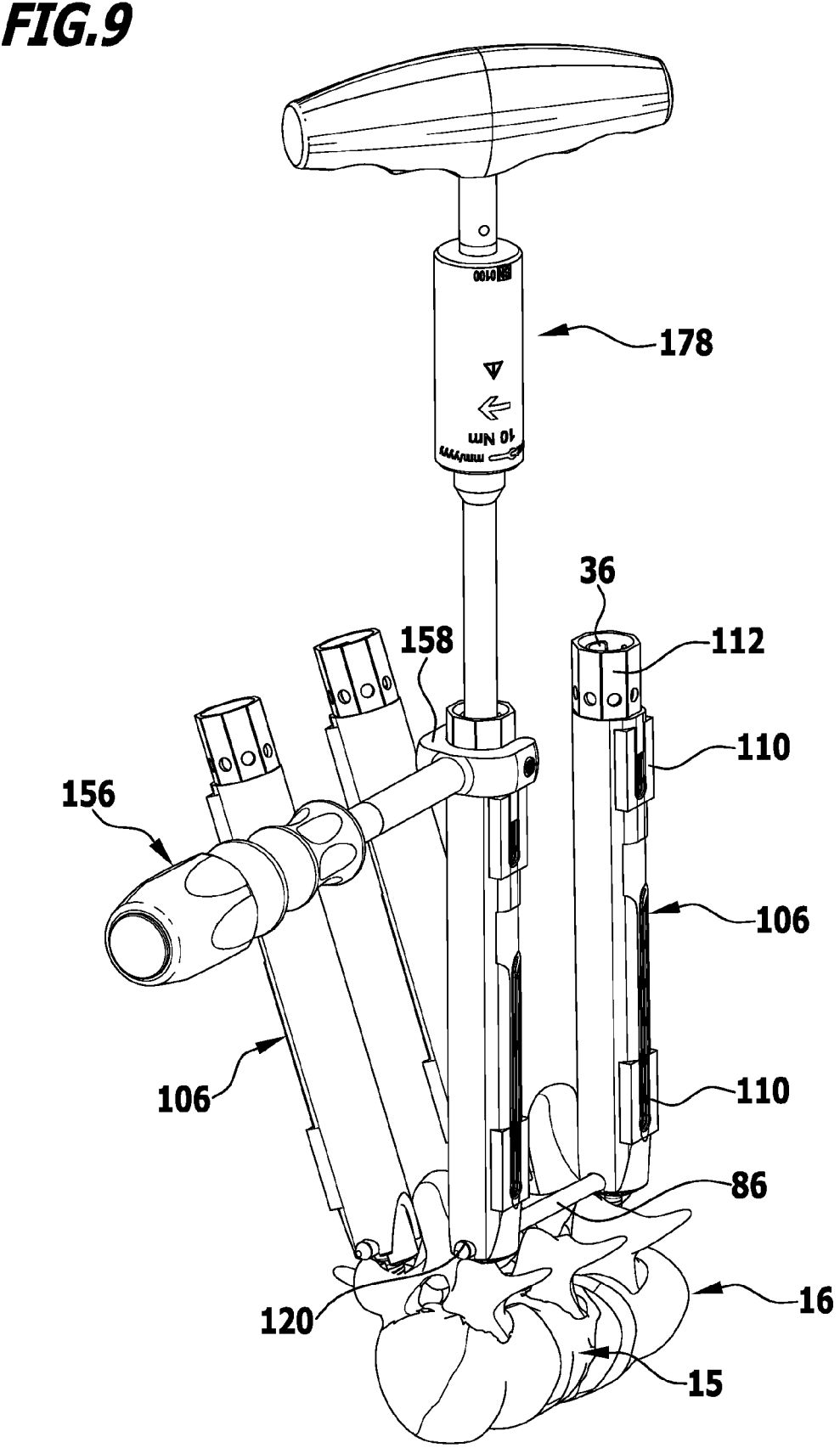
Figure 10:
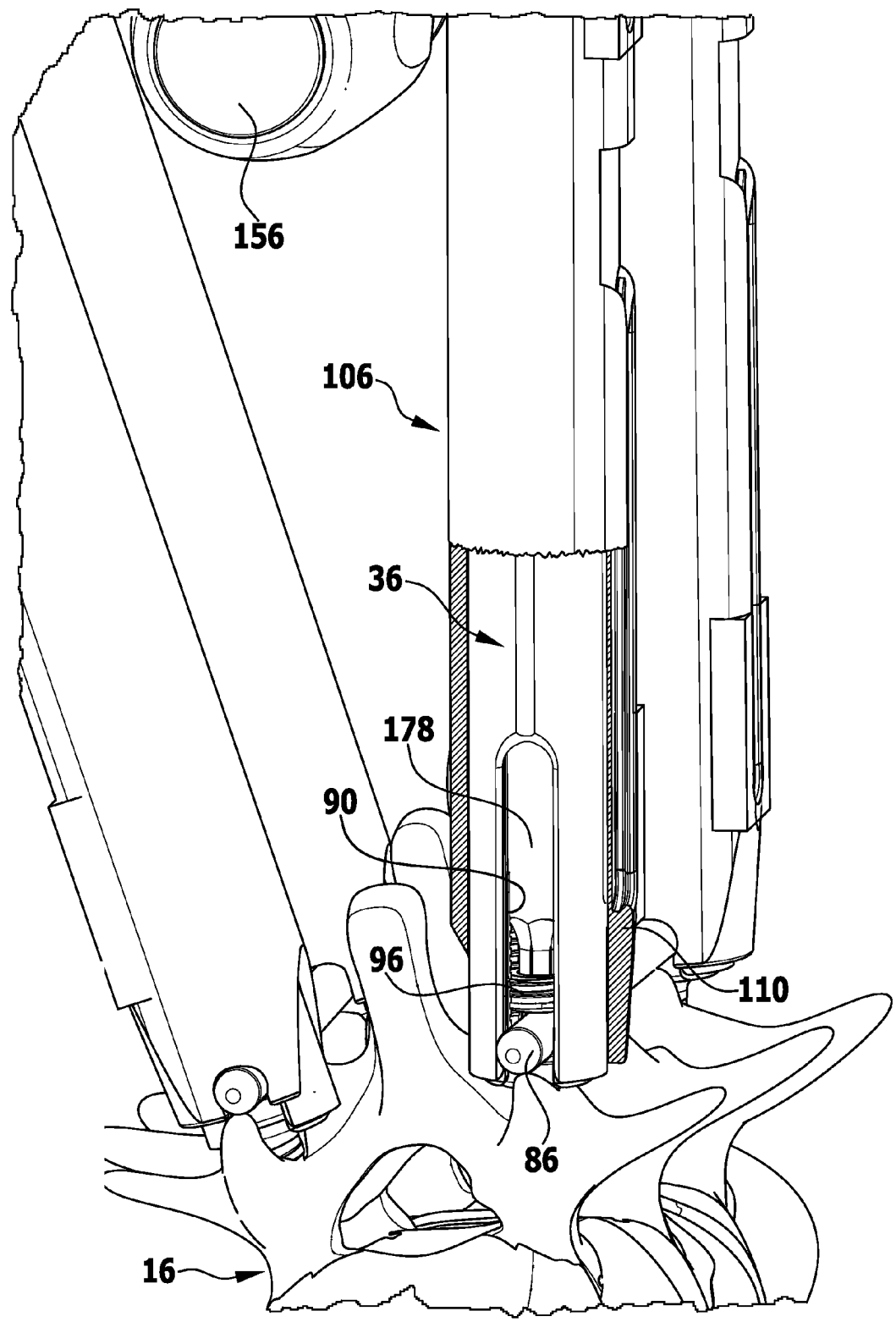
Figure 11:
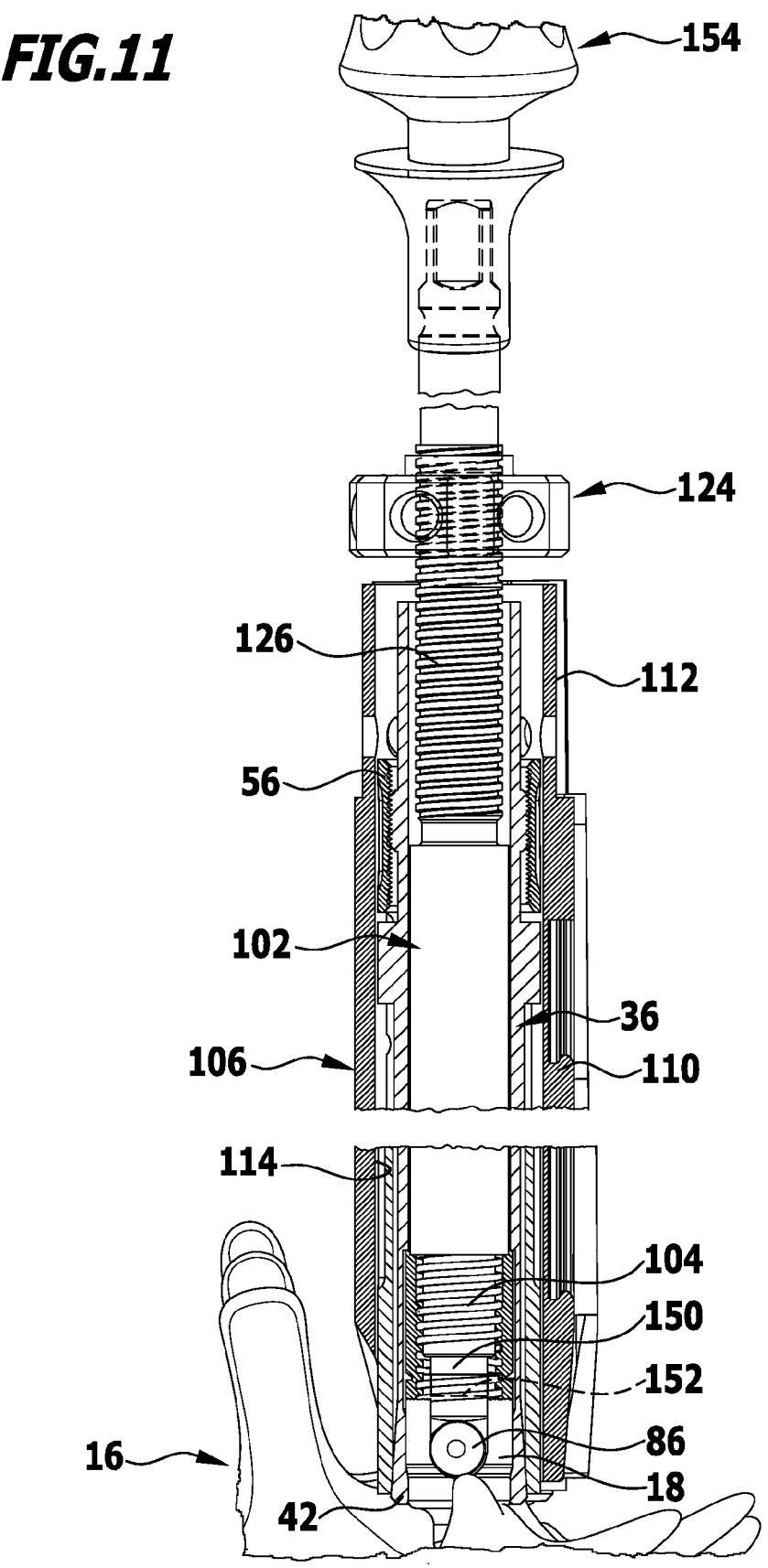
Figure 12:
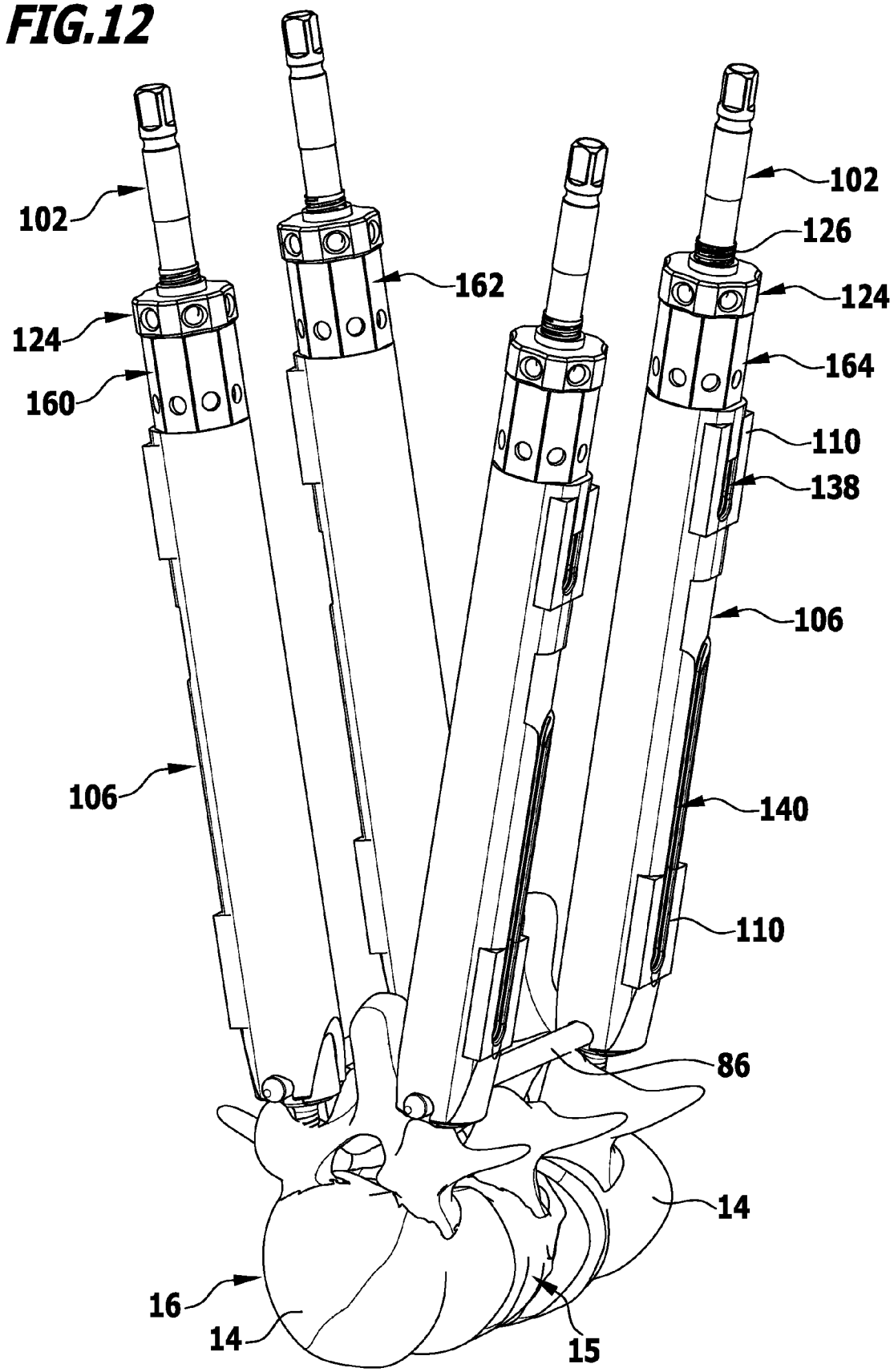
Figure 13:
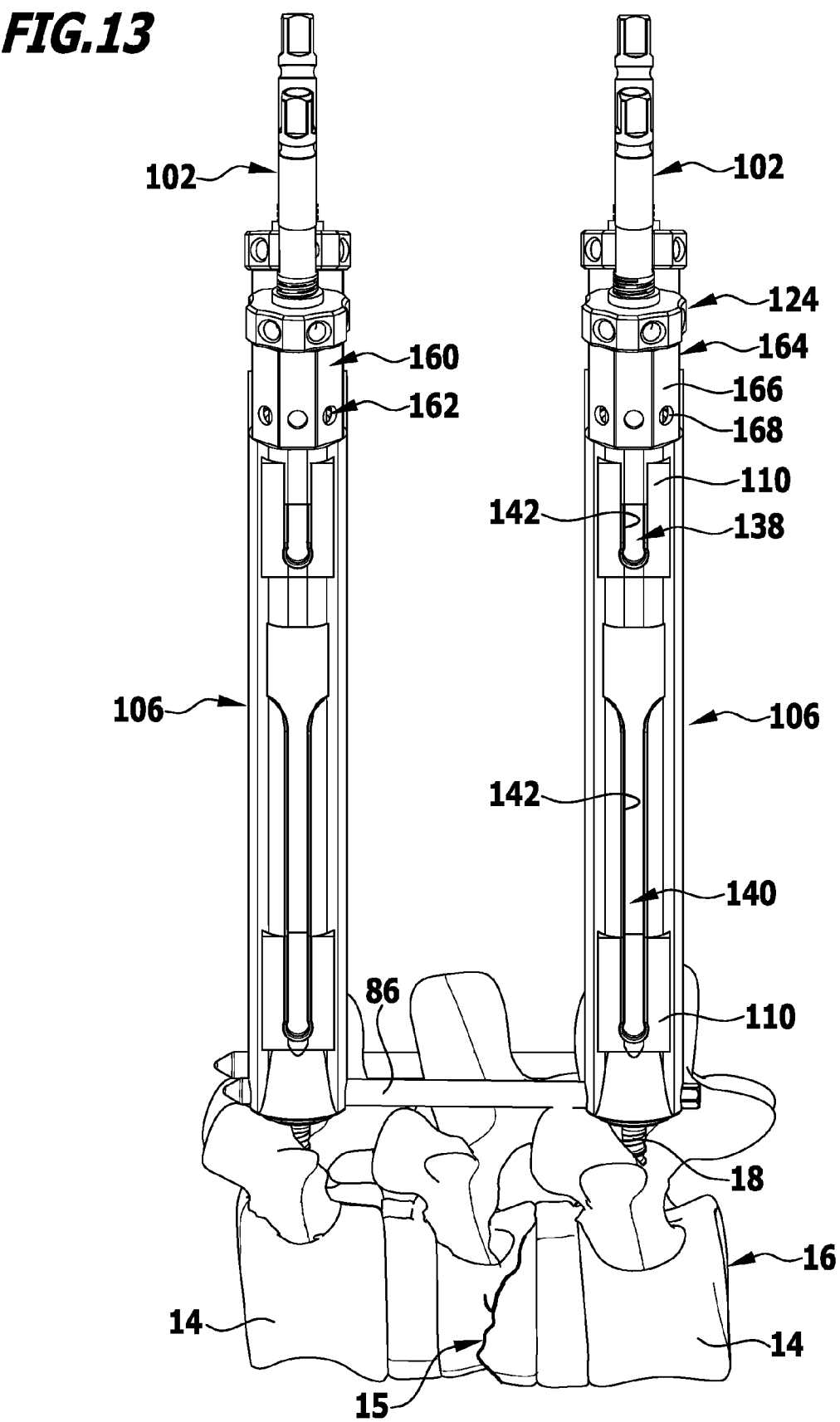
Figure 14:
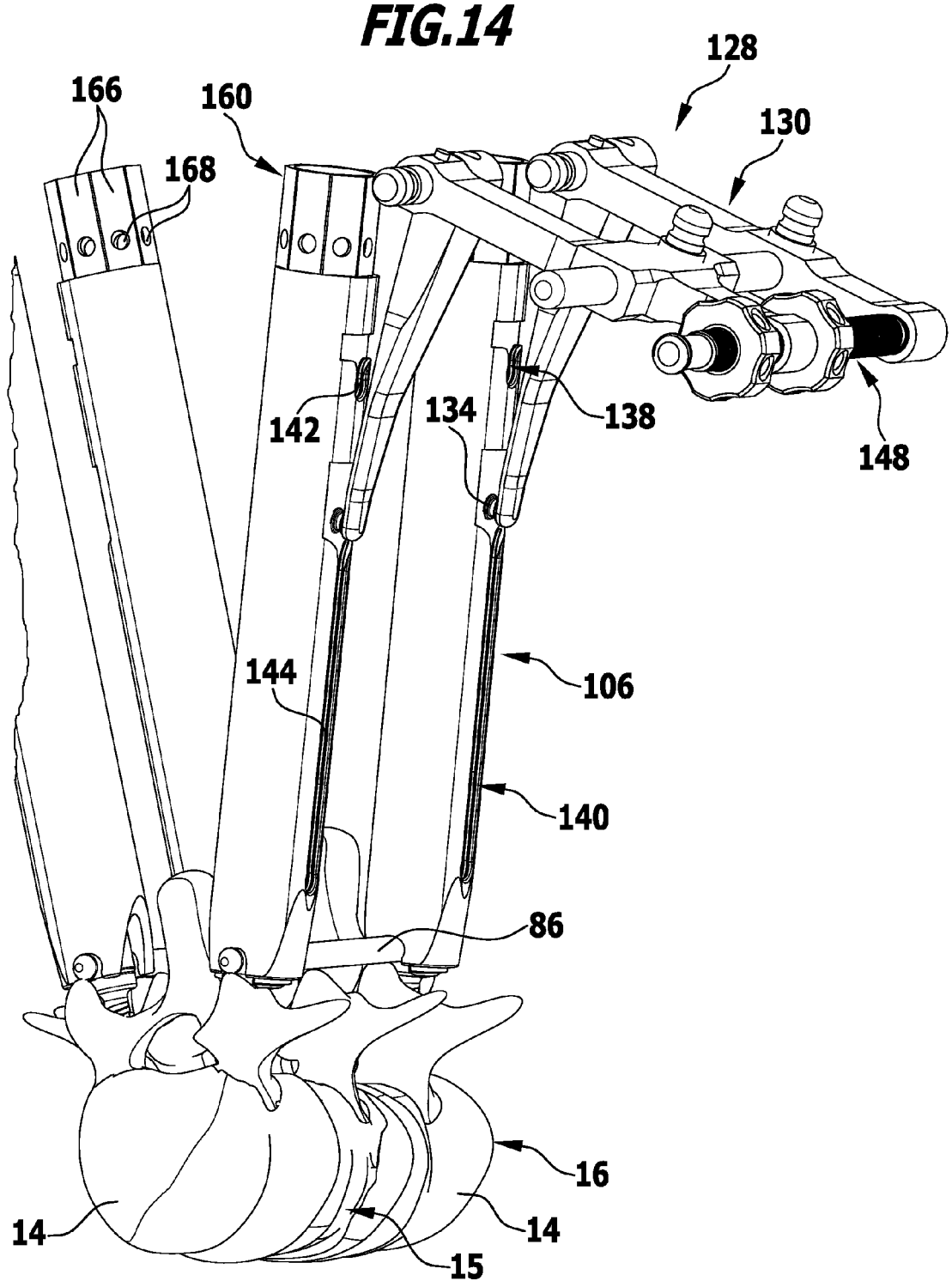
Figure 15:
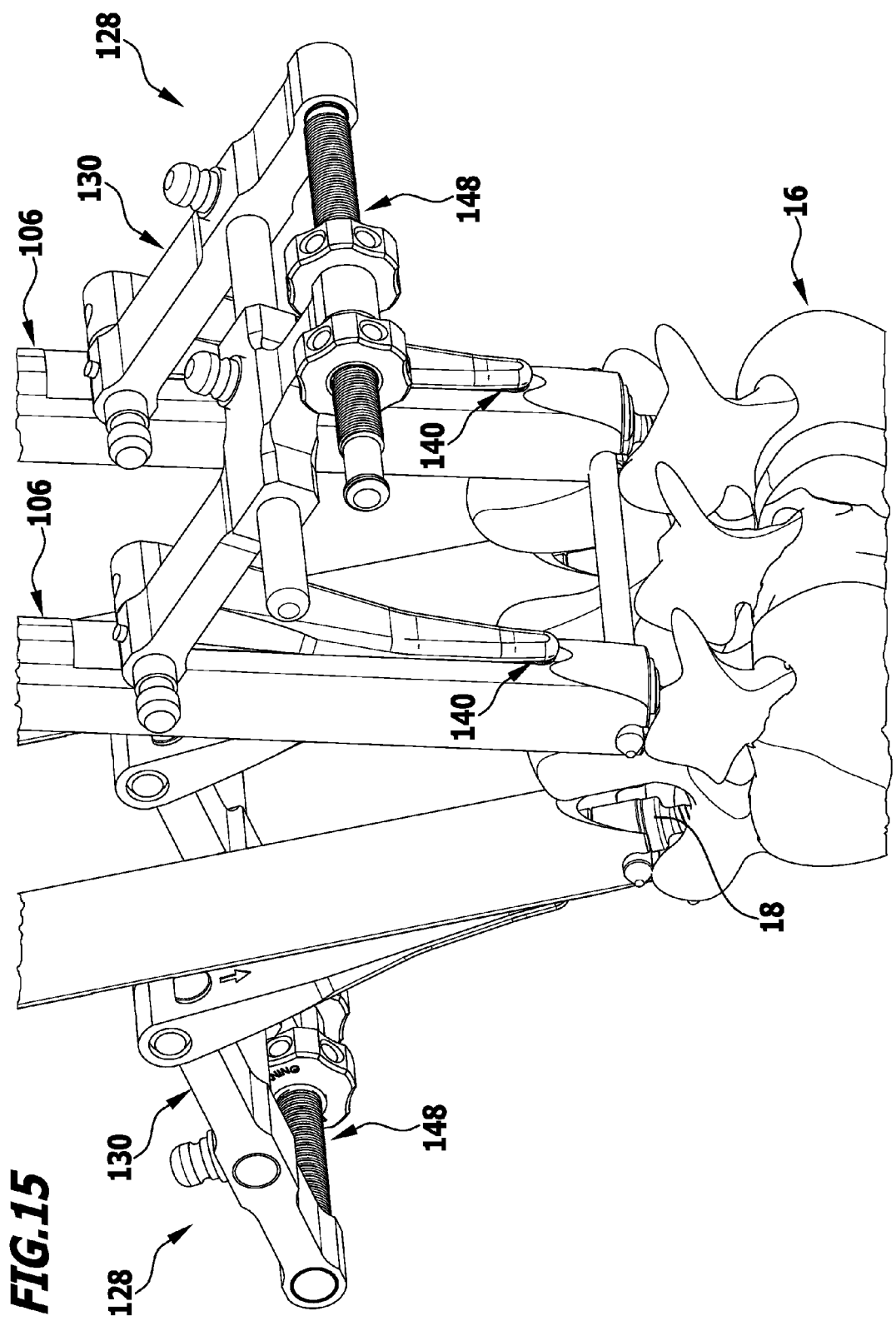
Figure 16:
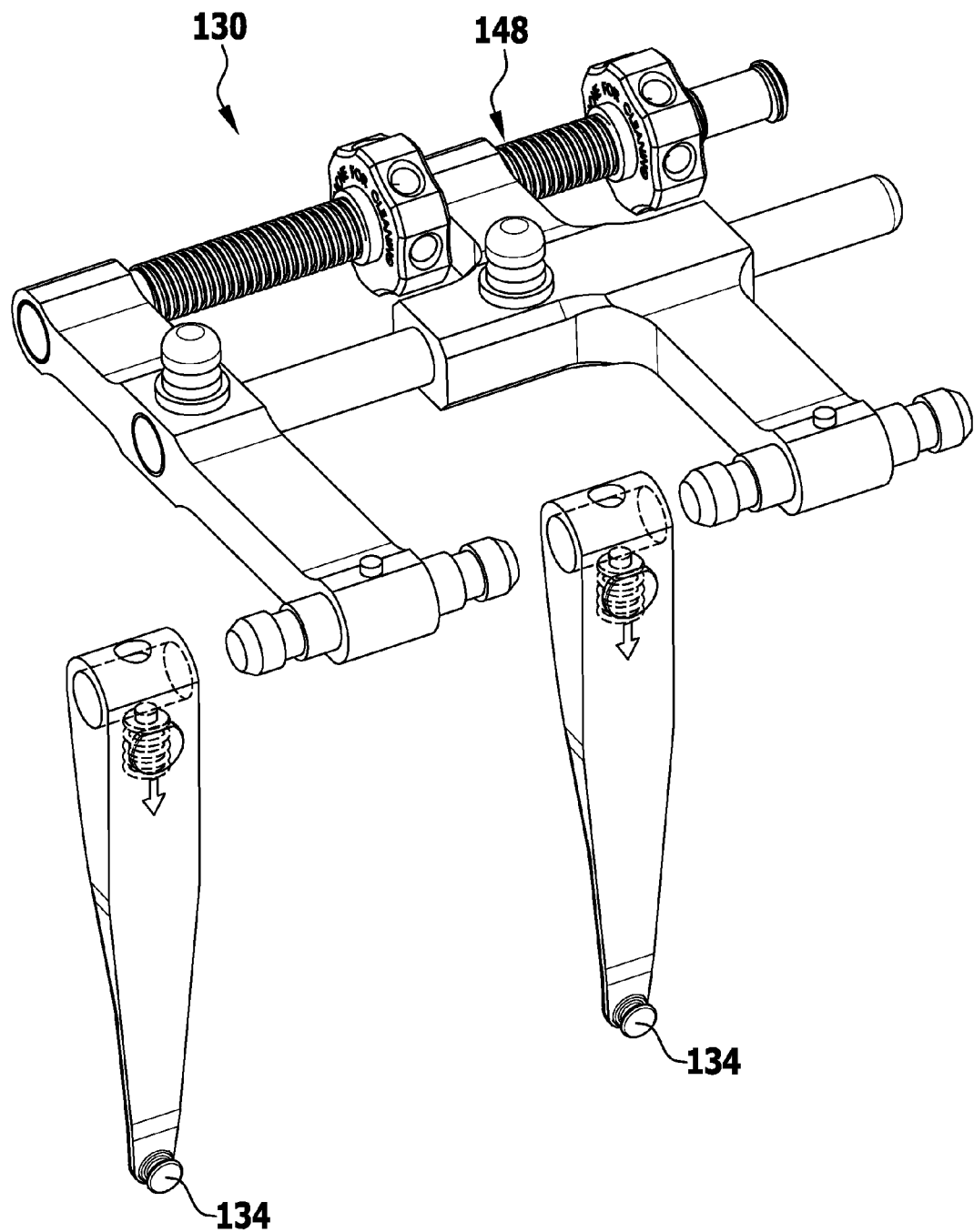
Figure 17:
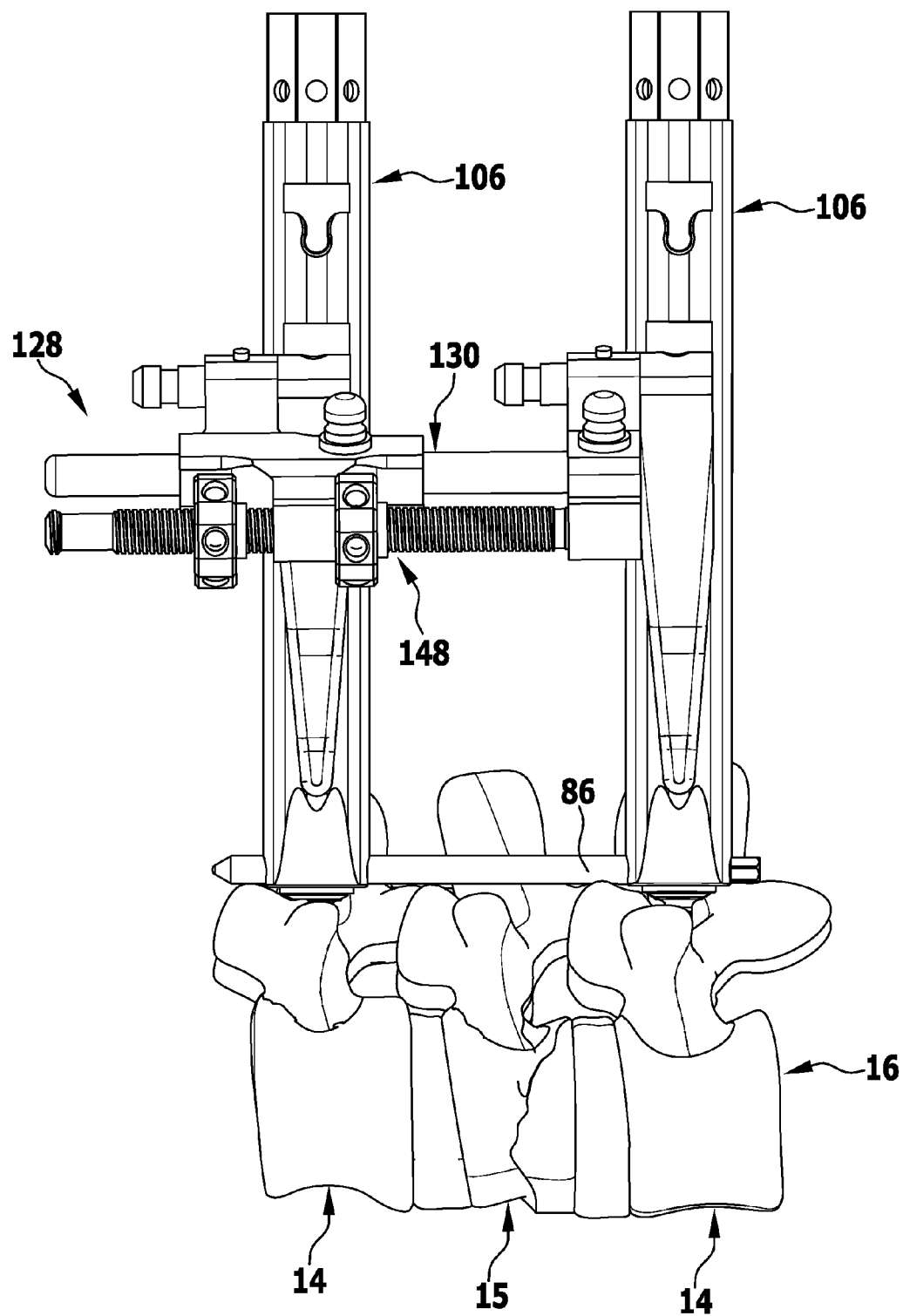
Figure 18:
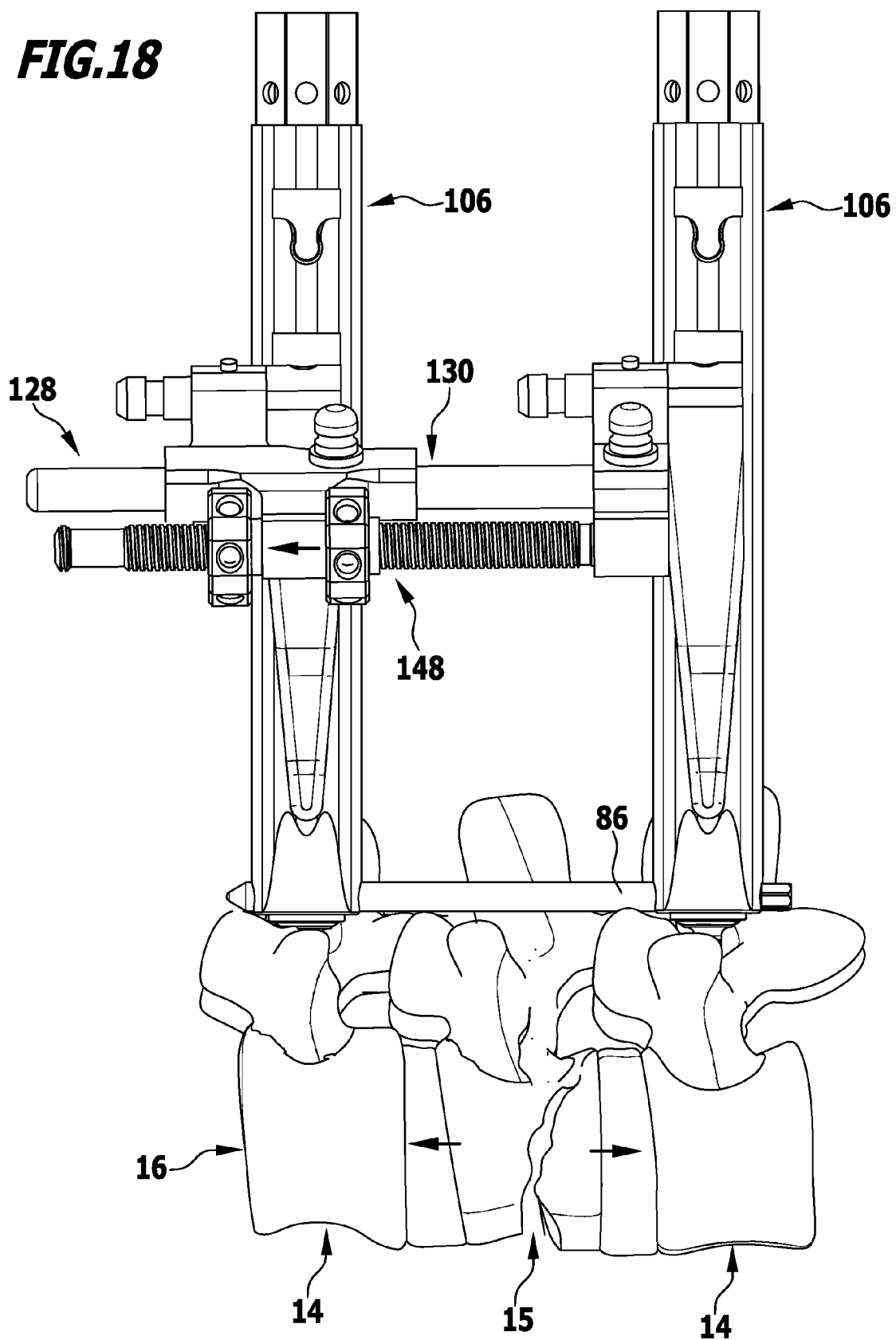
Figure 19:
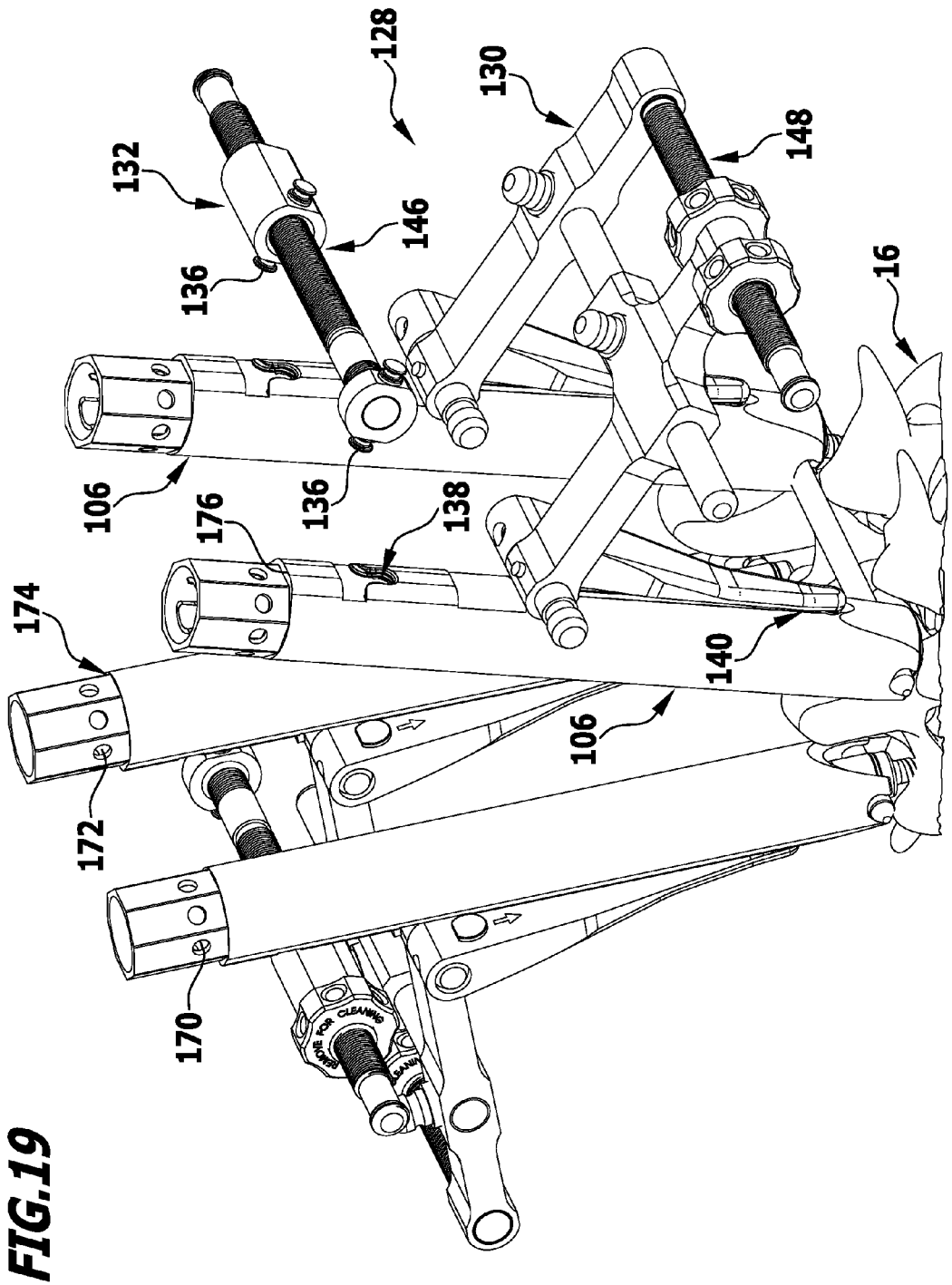
Figure 20:
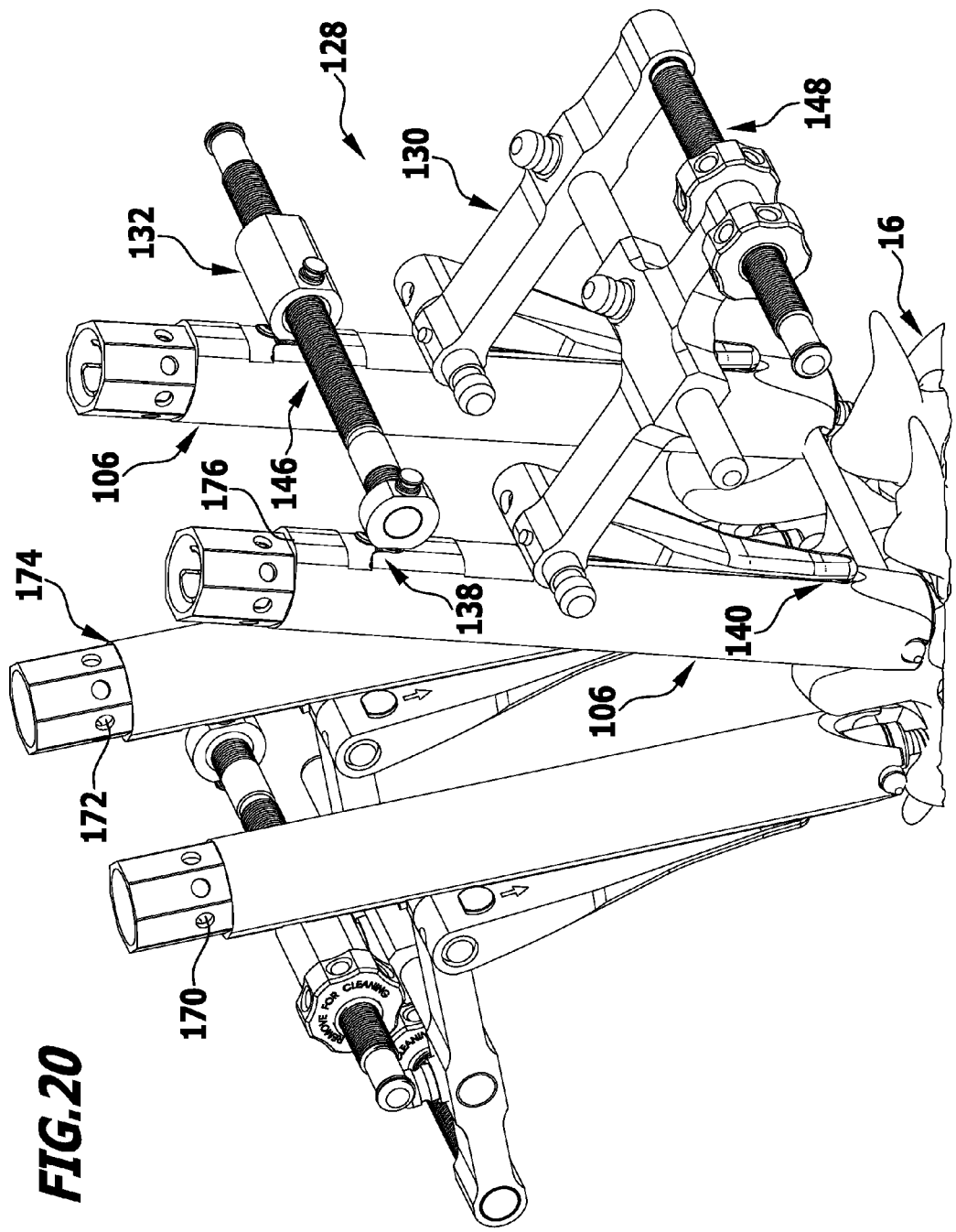
Figure 21:
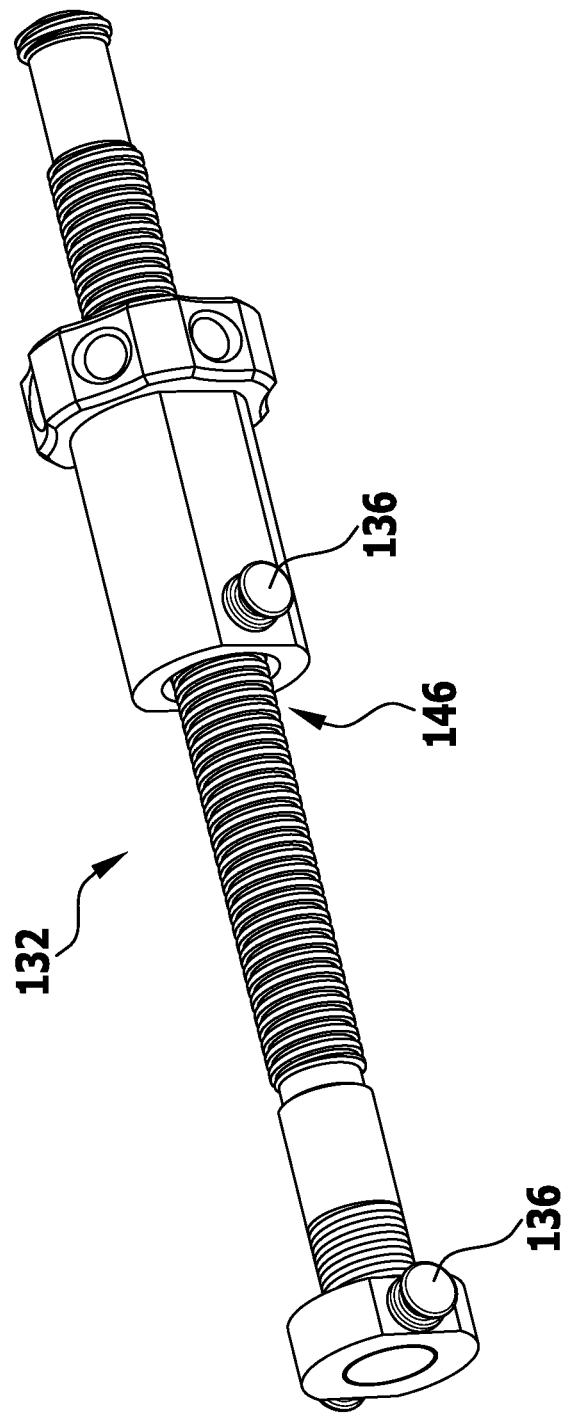
Figure 22:
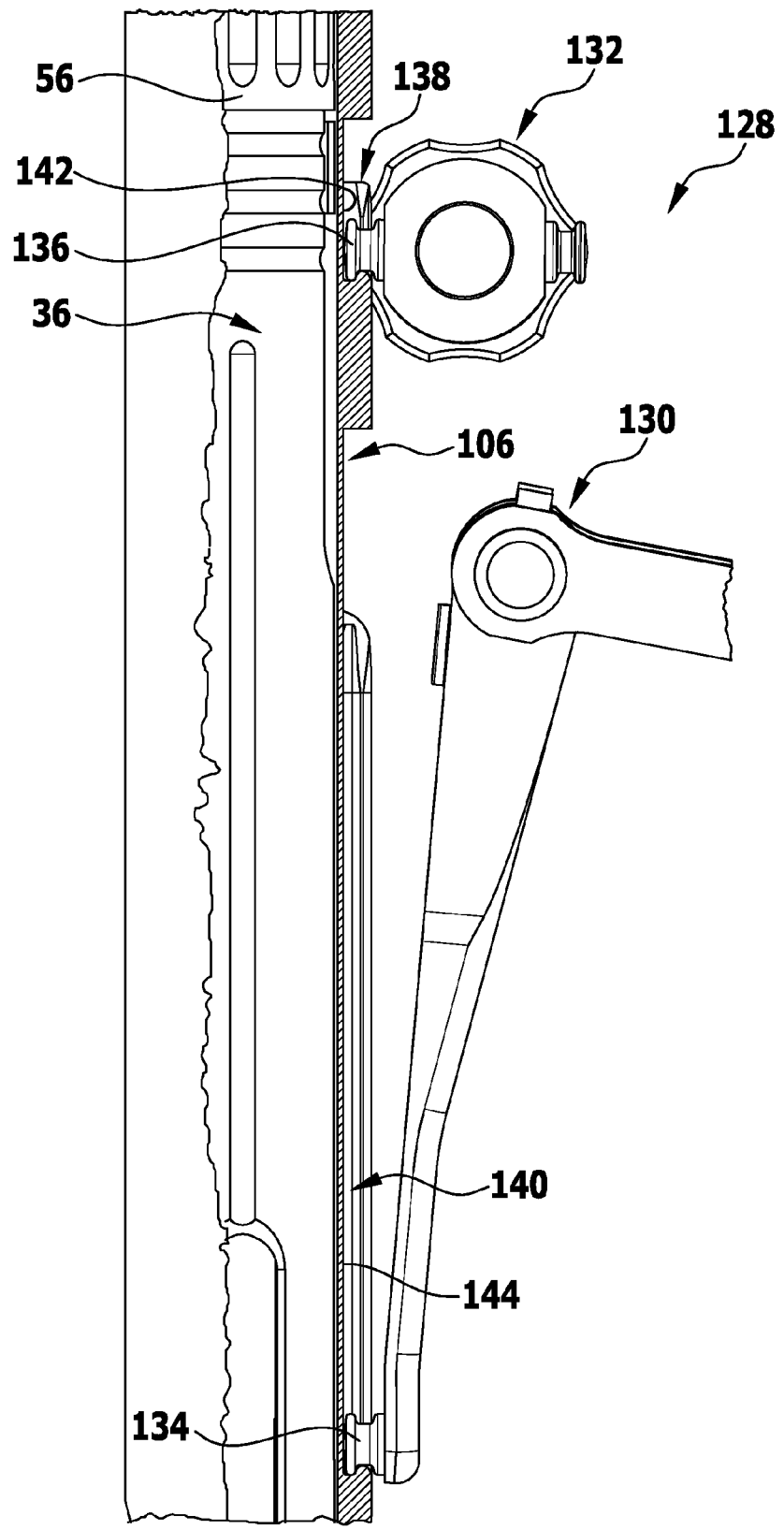
Figure 23:
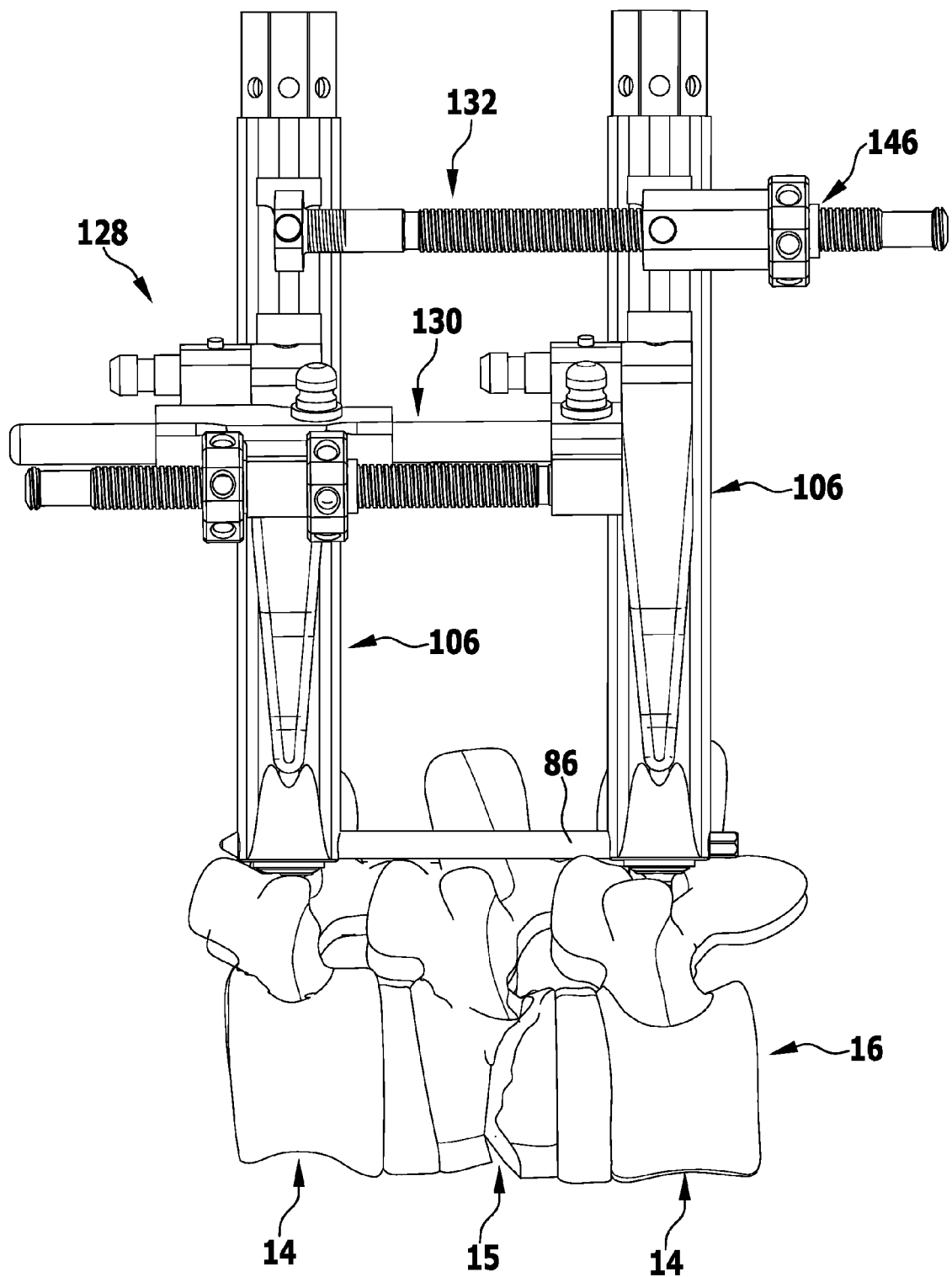
Figure 24:
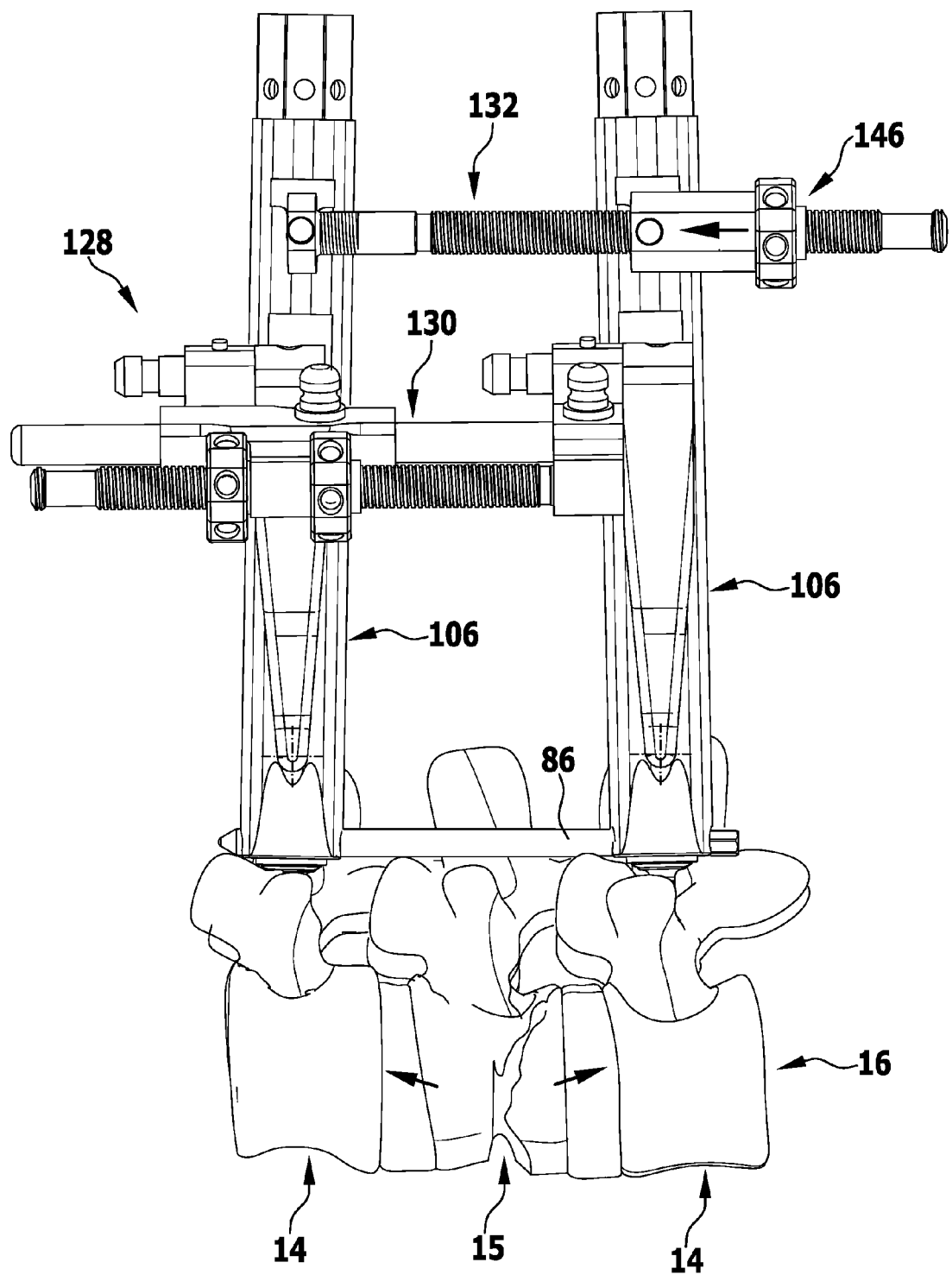

The foregoing summary and the following description may be better understood in conjunction with the drawing figures, of which:

FIG. 1: shows a schematic exploded illustration of the two-piece clamping sleeve;

FIG. 2: a schematic perspective view of the installed clamping sleeve as well as a mono-axial bone screw;

FIG. 3: a longitudinal sectional view of the clamping sleeve coupled in clamped manner to the head of the bone screw;

FIG. 3A: an enlarged view of the region A in FIG. 3;

FIG. 3B: an enlarged view of the region B in FIG. 3;

FIG. 4: a schematic illustration of the step of screwing-in a bone screw through a tissue protective sleeve over a K-wire;

FIG. 5: a schematic view of the clamping sleeve inserted into the tissue protective sleeve with a screw driving instrument after the process of screwing the bone screw into the vertebra;

FIG. 6: a schematic overall view of four screws coupled to a clamping sleeve when measuring and using a rod-like connecting element;

FIG. 7: a schematic illustration of the pre-assembly of a locking screw in the head of a bone screw;

FIG. 8: a schematic overall view of multi-function sleeves pushed over the clamping sleeves as well as of a multi-function sleeve when being pushed onto a clamping sleeve;

FIG. 9: a schematic overall view when fixing the locking screw in the head of the bone screw by means of a torque wrench and simultaneously holding down the multi-function sleeve by means of a holding instrument;

FIG. 10: a schematic, partly cut-away overall view when screwing the fixing screw into the head of the bone screw;

FIG. 11: a schematic sectional view when screwing-in the fixing screw with a fixing nut for fixing the multi-function sleeve to the clamping sleeve coupled in clamped manner to the bone screw;

FIG. 12: a schematic overall view of four inserted bone screws with mounted connecting elements and emplaced multi-function sleeves;

FIG. 13: a side view of the vertebral bodies prepared for a repositioning process;

FIG. 14: a schematic overall view when coupling a spreading device to two multi-function sleeves;

FIG. 15: a schematic overall view of the arrangement depicted in FIG. 14 with two coupled spreading devices;

FIG. 16: a schematic exploded illustration of a lower spreader of the spreading device in the form of a linear distractor of the spreading device;

FIG. 17: a schematic side view of the lower linear distractor coupled to two multi-function sleeves;

FIG. 18: a view similar to FIG. 17 when repositioning the two vertebral bodies;

FIG. 19: a schematic overall view of the arrangement depicted in FIG. 15 with two upper spreaders of the spreading device in the form of angular spindle distractors;

FIG. 20: a schematic view similar to FIG. 19 when inserting an upper angular spindle distractor into the seating of a spreading-device coupling device;

FIG. 21: a schematic enlarged overall view of an upper angular spindle distractor;

FIG. 22: a schematic, partly sectional side view of a multi-function sleeve which is coupled to a lower linear distractor and an upper angular spindle distractor;

FIG. 23: a schematic side view of two multi-function sleeves which are coupled to a lower linear distractor and an upper angular spindle distractor; and FIG. 24: a view similar to FIG. 23 when adjusting the angle of inclination between longitudinal axes of the bone screws by means of the upper angular spindle distractor.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical apparatus for the implantation of a spinal column stabilization system, which spinal column stabilization system comprises at least two bone screws which are respectively anchorable in a vertebra of a spinal column and which respectively comprise at least one first connecting element seating, and at least one connecting element which corresponds to the first connecting element seating and is insertable and fixable therein, wherein the apparatus comprises at least one multi-function sleeve having a proximal and a distal end, which multi-function sleeve defines a longitudinal axis and comprises a connecting element coupling device, a spreading-device coupling device and a holding instrument coupling device, wherein the multi-function sleeve comprises an internal wall surface which is rotationally symmetrical with respect to the longitudinal axis, and wherein no projections protrude from the internal wall surface or beyond it in the direction of the longitudinal axis.

In a surgical apparatus that has been further developed in such a manner, it is possible to utilise the multi-function sleeve thereof whilst the bone screw is still coupled to an insertion instrument such as a screwing-driving tool for example. In contrast to the multi-function sleeve that is known from U.S. Pat. No. 7,922,731 B2, the multi-function sleeve proposed in accordance with the invention cannot be brought directly into engagement with the forklike head of the bone screw, but rather, only indirectly, namely, by means of the connecting element coupling device with the connecting element inserted into the first connecting element seating. In this way, it is possible to hold the multi-function sleeve by the holding instrument coupling device whereby a holding torque is not introduced directly via the head of the bone screw as is the case for the apparatus known from U.S. Pat. No. 7,922, 731 B2, but rather, indirectly via the connecting element. This thus results in a completely different force flow and in particular has the advantage that the insertion instrument can be used as a means for protecting the bone screw during the entire procedure and also, in particular, as a guide for carefully introducing the multi-function sleeve into the body of the patient through the minimally invasive access and introducing the connecting element in the desired manner into the first connecting element seating with the multi-function sleeve and holding it therein, namely in particular, until a fixing or a locking screw for example is screwed into the head of the bone screw formed in forklike manner by the first connecting element seating with the aid of a further screw-driving instrument in order to fix the connecting element in the first connecting element seating. Due to the multi-function sleeve, which does not incorporate projections that protrude from the wall surface in the direction of the longitudinal axis or protrude beyond the wall surface in the direction of the longitudinal axis, it is possible to save at least one operational step namely, the removal of the pressing or holding-down instrument for the connecting element and the subsequent laborious task of bringing the multi-function sleeve into engagement with the head of the bone screw. Thus, as a result, the handling of the apparatus is simplified whereby errors can be avoided during the operational procedure and in addition, the latter can be accomplished more quickly. In particular, without directly viewing the site of the operation, it is now possible for an operating surgeon to not only safely introduce the connecting element into the first connecting element seating but also to fix it as desired to the bone screws in a defined manner significantly more easily and more rapidly without sight of the site of the operation.

It is expedient if the internal wall surface is circular in cross section and has a constant internal diameter parallel to the longitudinal axis. A multi-function sleeve formed in this way is producible in a simple manner, for example, by providing a boring in a rod-shaped shaft. In other words, the internal wall surface is thus in the form of an elongated hollow cylinder in particular.

The production and construction of the multi-function sleeve can be further simplified, if it is formed such as to be symmetrical with respect to a plane containing the longitudinal axis. Thus in particular, it can be formed such as to be mirror-symmetrical with respect to this plane.

It is advantageous if the connecting element coupling device is arranged or formed at the distal end of the multi-function sleeve such as to be coupled to the connecting element in mutually non-rotational manner. It is especially expedient if the connecting element engages in the first connecting element seating of two bone screws. With such a form of connecting element coupling device arranged on the multi-function sleeve in this manner, the connecting element can easily be pressed securely into the first connecting element seating of the bone screws in the desired way and also held therein.

In accordance with an embodiment of the invention, provision may be made for the connecting element coupling device to comprise at least one second connecting element seating which is configured such as to be brought into engagement with the at least one connecting element in force- and/or shape-locking manner. In particular, provision may be made for two second connecting element seatings in which the connecting element can engage in order to thereby establish a coupling between the multi-function sleeve and the connecting element that is non-rotational with respect to the longitudinal axis. In this way in particular, the connecting element can be introduced into the first connecting element seating of the bone screws in a defined manner and at the same time too, a holding torque cannot be introduced directly to the head of the bone screws by the multi-function sleeve, but rather, indirectly via the connecting element inserted into the first connecting element seating.

Furthermore it is expedient if the at least one second connecting element seating comprises a recess which, commencing from the distal end, is formed in a sleeve wall of the multi-function sleeve and is open in the distal direction. The connecting element can thus be introduced directly into the first connecting element seating by the distal end of the multi-function sleeve and held therein.

It is advantageous if the spreading-device coupling device is in the form of a releasable connection to a spreading device for moving the two bone screws relative to each other. In particular, the spreading device can be formed such as to move the bone screws in a direction away from each other, for example, for restoring the vertebrae into their original position or into the position desired by the operating surgeon. Thus, in the case of fractured vertebrae in particular, not only can stabilization be achieved, but one can also obtain the desired relative positioning of the vertebrae in order to relieve, in particular, the spinal cord as well as the nerves of the patient.

The multi-function sleeve can be coupled to a spreading device in a particularly simple way if the spreading-device coupling device comprises at least one coupling seating which is arranged on an outer surface of the multi-function sleeve. The spreading device can thus be brought temporarily into engagement, in particular laterally, with two multi-function sleeves coupled to bone screws inserted into vertebrae neighbouring a damaged vertebra in order to move the vertebrae and hence too the spinal column back into their desired position.

The at least one coupling seating can be formed in a particularly simple way if it comprises a groove which extends in parallel with a longitudinal axis defined by the multi-function sleeve. In particular, the groove can be undercut laterally transverse to the longitudinal axis on both sides. Thus, for example, the spreading device can be provided with connecting studs having a T-shaped cross section in order to be brought into engagement with the undercut groove.

The spreading device can be coupled to the multi-function sleeves in a particularly simple way if the at least one coupling seating is open in the direction of the proximal end for the insertion of a coupling stud of the spreading device.

In order to enable spreading forces to be introduced into the multi-function sleeves in a particularly defined way, it is expedient if the multi-function sleeve comprises two coupling seatings, wherein the one coupling seating is arranged or formed in the region of the distal end and wherein the other coupling seating is arranged or formed in the region of the proximal end. A relatively torsionally stiff coupling between the spreading device and the multi-function sleeves can thereby be achieved in order to move the bone screws and hence the vertebrae connected thereto relative to each other without torsional moments insofar as possible. Moreover, as an option, both the spacings of the bone screws from each other and an inclination thereof relative to each other can be set.

Preferably, the spreading-device coupling device comprises at least one stop acting in the proximal direction. The spreading device can thus be prevented from moving too far in the distal direction whereby soft tissue could be damaged.

The multi-function sleeve is producible in a particularly simple manner if the at least one stop comprises a projection which is arranged on an outer surface thereof and has at least one stop surface facing in the proximal direction.

In accordance with an embodiment of the invention, provision may be made for the holding instrument coupling device to be arranged or formed at the proximal end of the multi-function sleeve for connecting it to a holding instrument in releasable mutually non-rotational manner. For example, the holding instrument may be in the form of a bracing handle which has a shape corresponding to the holding instrument coupling device for enabling a temporary shape-locking connection to be made thereto.

The holding instrument coupling device can be formed in a particularly simple manner if it comprises a polyhedron which forms an end section of the multi-function sleeve defining the proximal end. Typically, in a minimally invasive procedure, the proximal end of the multi-function sleeve protrudes from the body of the patient so that when necessary, namely particularly when tightening the fixing or locking screw for fixing the connecting element to the head of the bone screws, an operating surgeon, with the holding instrument on the multi-function sleeve, can introduce a torque countering the screwing-in torque in order to prevent unwanted distortion of the bone screw and a change in the position thereof in the vertebra that is entailed thereby. Preferably, the polyhedron is in the form of a hexagon or an octagon.

It is expedient if the polyhedron defines flat outer surfaces and if at least one of the outer surfaces incorporates a holding recess facing away from the longitudinal axis. For example, provision may be made for corresponding projections in the form of e.g. ball thrust pieces on the holding instrument in order to provide defined coupling to the polyhedron and prevent unwanted slippage thereof whilst held-down during the process of fixing the connecting element.

Expediently, the holding recess is in the form of a through opening passing through a sleeve wall of the multi-function sleeve. The through opening can, in particular, be in the form of a boring.

Furthermore, it can be advantageous if the multi-function sleeve has a polyhedral stop which adjoins the polyhedron on the distal side and comprises at least one polyhedral stop surface facing in the proximal direction. In particular, the polyhedral stop serves to prevent the holding instrument from slipping off the polyhedron in the distal direction.

In order to permit as defined a force as possible to be applied by a holding instrument to the multi-function sleeve, it is advantageous if the holding recess is arranged and formed closer to the polyhedral stop than to the proximal end of the multi-function sleeve. The holding instrument can then be supported on the polyhedral stop when it is in engagement with two holding recesses for example. A counter-holding moment can thereby be introduced in a particularly certain manner.

Particularly for the purposes of improving the stability of the multi-function sleeve, it is advantageous if it is formed in one piece manner.

In accordance with a further preferred embodiment, provision may be made for the apparatus to comprise at least one clamping sleeve for producing a clamped connection to a head of one of the bone screws. In particular, the at least one clamping sleeve can be formed so as to connect a distal end thereof to a head of the bone screw in clamped manner. With the aid of such a clamping sleeve, it is possible to produce a clamped connection to the bone screw and to insert it into the vertebra by means of the clamping sleeve, optionally even by screwing it in, by the cooperation of the clamping sleeve with a further instrument for example. In particular, the clamping sleeve thereby forms a holding tool and/or a screw-driving tool for a bone screw.

It is advantageous if the exterior of the clamping sleeve is dimensioned in such a manner that it is insertable at least partially, especially entirely, into the multi-function sleeve and is rotatable about the longitudinal axis relative thereto. A clamping sleeve formed and dimensioned in such a manner simultaneously enables it to function as a guide sleeve for the introduction of a distal end of the multi-function sleeve, and hence the whole multi-function sleeve, into the body of the patient through a minimally invasive access. In particular, the multi-function sleeve can be displaced, until such time as it comes into engagement by means of the connecting element coupling device with the connecting element, not only axially relative to the clamping sleeve, but it can also be rotated about the longitudinal axis relative thereto. This facilitates alignment of the multi-function sleeves and in particular the spreading-device coupling devices thereof relative to each other.

Furthermore, it is advantageous if the clamping sleeve comprises an outer sleeve and an inner sleeve that is insertable into the outer sleeve and in particular, if the outer sleeve is insertable into the multi-function sleeve. A defined clamped-connection to a head of the bone screw can be achieved by the two-piece structure of the clamping sleeve. In addition, it is simpler in this way, to remove the clamping sleeves from the bone screws after the implantation of the spinal column stabilization system.

Moreover, it is expedient, if the surgical apparatus comprises at least one K-wire target device, a K-wire, a tissue protective sleeve, a dilation sleeve, a pedicle awl, a thread cutter for cutting a thread in a sclerotic bone, a rod length measuring instrument and/or a screw length measuring instrument. In particular, the listing means that all conceivable combinations of the elements mentioned can be components of the apparatus. Furthermore, as will be described in detail below, bone screws can be inserted easily and securely into a vertebra with these instruments.

In order to have to make as few changes of individual instruments of the apparatus as possible during the surgical procedure, it is advantageous if the K-wire target device is insertable into the dilation sleeve and/or if the dilation sleeve is insertable into the tissue protective sleeve. Thus for example, the tissue can initially be dilated by means of the dilation sleeve and the tissue protective sleeve subsequently pushed over the dilation sleeve. After removing the dilation sleeve, the tissue protective sleeve can then serve as a guide, in particular, for working on the vertebrae with the pedicle awl or the thread cutter. Furthermore, the lengths of the necessary screws can also be determined through the tissue protective sleeve by means of the screw length measuring instrument. Furthermore, the clamping sleeve can be introduced through the tissue protective sleeve after it is coupled to the bone screw in order to screw the bone screw into the bone by means of a screwdriver inserted through the clamping sleeve.

A surgical apparatus 10 for implanting a spinal column stabilization system 12 is illustrated exemplarily in FIGS. 1 to 24.

The spinal column stabilization system 12 comprises at least two bone screws 18 which are respectively anchorable in a vertebra 14 of a spinal column 16 and each of which has a shaft 20 that is provided with a preferably self-cutting external thread and a head 22 that is immovable relative to the shaft and is in the form of a head sleeve 24 which is provided with an internal thread 26 and two lateral slots 30 defining a first connecting element seating 28. A peripheral groove 32 in the head sleeve 24 forms a break-off section which is interrupted by the slots 30. Thus, overall, the bone screws 18 are in the form of mono-axial screws which define a longitudinal axis 34. The head sleeve 24 is arranged to be concentric with the longitudinal axis 34, the shaft 20 likewise.

For the purposes of holding and guiding each of the bone screws 18, there serves a clamping sleeve 36 which comprises an inner sleeve 38 and an outer sleeve 40. The inner sleeve 38 has a clamping cone 42 at its distal end and, commencing from the distal end, it is divided into two resilient sections 48 by a slot extending in the direction of a longitudinal axis 44. Two recesses 50 are formed in a wall of the inner sleeve 38 commencing from a proximal end thereof. Somewhat on the distal side of the recesses 50, there is formed an externally threaded section 52 which corresponds to an internal thread 54 of a knurled nut 56.

Somewhat on the distal side of the externally threaded section 52, there are two diametrically opposed guidance projections 58 which point away from each other in the radial direction and protrude from an outer wall surface of the inner sleeve.

The outer sleeve 40 is dimensioned such that the inner sleeve 38 can be pushed into the outer sleeve 40 from the proximal end with the clamping cone 42 in front. Commencing from the distal end thereof, the outer sleeve 40 has slots 60 which are mutually diametrically opposite with respect to the longitudinal axis 44 and extend over approximately a quarter of the overall length of the outer sleeve 40. Commencing from the proximal end of the outer sleeve 40, there are also provided two diametrically opposed slots 62. These are just broad enough to accommodate the guidance projections 58 so that the inner sleeve 38 is then prevented from twisting relative to the outer sleeve 40 when the guidance projections 58 engage in the slots 62.

Preparatory to assembly of the clamping sleeve 36, the distal end of the knurled nut 56 is firstly screwed down to the lower thread of the externally threaded section 52. The proximal end of the inner sleeve 38 is then pushed into the outer sleeve 40. The clamping cone 42 then protrudes beyond the distal end of the outer sleeve 40 as is illustrated schematically in FIG. 2. The thus prepared clamping sleeve 36 can now be pushed from the proximal end thereof over the head sleeve 24 by means of the clamping cone 42, namely until a proximal end of the head sleeve 24 strikes a step 64 which is formed in the interior of the inner sleeve 38 and faces in the distal direction. An internal contour of the clamping cone 42 matches an outer contour of the head sleeve 24 which tapers in the distal direction so that as a consequence of further rotation of the knurled nut 56 in the distal direction, the clamping cone 42 slides over an inner surface of the outer sleeve 40 in the region of the slots 60, whereby the sections 48 are swung somewhat in the direction of the longitudinal axis 44 and the head sleeve is thereby held between the step 64 and the clamping cone 42 in clamped manner. The knurled nut 56 is rotated further in the distal direction until it strikes the guidance projections 58, as is exemplarily illustrated in FIG. 3A. The compression joint between the clamping sleeve 36 and the head 22, i.e. the cooperation of the inner sleeve 38, the outer sleeve 40 as well as the head sleeve 24, is illustrated exemplarily in FIG. 3B.

A tool-holder 66 facing in the proximal direction for a screw-driving tool 68 which is arranged at the distal end of a screw-driving instrument 70 is formed in the transition region between the head sleeve 24 and the shaft 20. Furthermore, the shaft 20 can be cannulated throughout its length i.e. provided with a thin longitudinal boring 72 through which a K-wire 74 can be fed.

In order to insert the bone screw 18 into the vertebra 14, it is first necessary to employ a guidance instrument which is not illustrated in the Figures and which comprises a trocar and a K-wire target device. It is preferably introduced at the transition from a facet of the vertebra 14 to the processus transversus. In the next step, the trocar or the trocar sleeve thereof is removed whereby the K-wire target device remains in the pedicle. For the purposes of guiding the cannulated bone screw 18, the K-wire 74 is now inserted through the K-target device and anchored in the vertebra 14. In order to prevent the K-wire 74 from swaying about or buckling, a K-wire-protective sleeve incorporating a longitudinal boring having an internal diameter adapted to the outer diameter of the K-wire 74 can optionally be used.

For the purposes of placing the bone screws 18, it is advantageous if the work area is firstly dilated with the aid of a dilation sleeve which is not illustrated in the Figures. This sleeve has an internal diameter which enables it to be pushed over the K-wire-protective sleeve and the K-wire target device.

In the next step, a tissue protective sleeve 76 is pushed over the dilation sleeve, namely up to the vertebra 14. An internal diameter of the tissue protective sleeve 76 widens out in slightly conical manner in the proximal direction. Furthermore, at the proximal end of the tissue protective sleeve 76 there is a ring flange 78 which projects from the longitudinal axis 44 in the radial direction and forms a kind of feed-in funnel for the easier introduction of further instruments of the apparatus 10. An internal diameter of the tissue protective sleeve 76 is dimensioned such that the clamping sleeve 36 with the bone screw 18 clamped thereon can be pushed through it in the distal direction.

However, before the bone screw 18 is introduced, the K-wire target device and then the dilation sleeve are first removed. In order to make it simpler to remove the K-wire target device, use can be made of a removal aid which can be coupled to a proximal end of the K-wire target device by means of a clamped connection in order to better grip the K-wire target device and enable it to be pulled away from the vertebra 14 in the proximal direction.

Optionally, the pedicle of the vertebra 14 can be prepared with a pedicle awl which is not illustrated in the Figures. This is also cannulated and is pushed over the K-wire 74 placed in the vertebra 14.

In particular for sclerotic bones, a thread cutter having a diameter corresponding to the bone screw 18 can be provided in order to facilitate the process of screwing-in the bone screws 18. The thread cutter too is preferably cannulated in order to advance it over the K-wire 74 to the vertebra and enable it to be prepared in a defined manner.

Optionally, for the purpose of determining the requisite length of screw, use is made of a screw length measuring instrument incorporating a scale which can be inserted over the K-wire and seated at the distal end thereof on the vertebra 14. The screw length can then be read off directly with the help of a central marking provided on the K-wire 74.

For the purpose of screwing-in the bone screw 18, the screw-driving instrument 70, which comprises two diametrically opposed stop studs 80 that project in the radial direction with respect to the longitudinal axis 44 in the vicinity of a proximal end thereof, is inserted through the clamping sleeve, namely, until the stop studs are inserted into the recesses 50 to the maximum extent. In this position, the screw-driving tool 68 then engages positively in the tool-holder 66. A shaft 82 of the screw-driving instrument 70 is likewise cannulated, i.e. it is provided with a longitudinal boring 84 that is coaxial with the longitudinal axis 44. The longitudinal boring 84 is matched to the outer diameter of the K-wire 74. The unit consisting of the clamping sleeve 36, the screw-driving instrument 70 and the bone screw 18 can now be inserted into the tissue protective sleeve 76 from the proximal end over the K-wire 74. The bone screw 18 is then screwed into the vertebra 14 by introducing a screw-driving torque directly into the head 22 of the bone screw 18 by means of the screw-driving instrument 70. The stop studs 80 serve as drivers and rotate the clamping sleeve 36, which is coupled to the head 22 in clamped manner, in synchronism with the bone screw 18. In order to facilitate the screw-driving process, a proximal end of the screw-driving instrument 70 can be optionally coupled to a handle.

For the treatment in the manner described of a vertebral fracture as illustrated schematically in FIG. 6, a total of four bone screws 18 are screwed into the vertebrae 14 neighbouring the fractured vertebra 15, i.e. two bone screws in each one of the two undamaged vertebrae 14. Furthermore, the K-wire 74 can now be removed.

Before withdrawing the screw-driving instrument 70, there first takes place a process of aligning the bone screws 18, namely, in such a manner that the first connecting element seatings 28 of two bone screws 18 are aligned relative to each other in order to enable a rod-shaped connecting element 86 to be introduced with the help of a rod-holding instrument 88, as is illustrated exemplarily in FIG. 6. This is facilitated, in particular, in that the recesses 50 are oriented in the same way as the slots 46 which expose the slots 30 in the head sleeve 24. Thus, in each unit consisting of a bone screw 18 and a clamping sleeve 36, there are defined two window openings 90 which are diametrically opposed with respect to the longitudinal axes 44 and through which the connecting element 86 can be passed. The rod-holding instrument 88 can, in particular, be in the form of a rod-holding instrument that is disclosed in U.S. Pat. No. 7,998,144 B2.

The necessary length of the connecting element 86 is determined with a rod length measuring instrument 92. To this end, two shafts of the rod length measuring instrument 92 are passed through the clamping sleeve 36 into the head 22. The necessary length can then be read off directly on a scale 94 of the rod length measuring instrument 92. If, however, a distraction is necessary, i.e. a movement away from one another of the two vertebrae 14 in which the bone screws 18 are anchored, then a correspondingly longer connecting element 86 must be selected. When using curved connecting elements 86, a reserve of about 10 mm has to be included in addition.

For the purposes of fixing the connecting element 86 to the heads 22, there is a respective locking screw 96 which has an external thread 98 corresponding to the internal thread 26. The locking screw 96 is screwed-in with a screwdriver 100, but is not yet tightened so tightly that a further relative movement of the connecting element 86 in the window openings 90 is still possible. The screwdriver 100 is then withdrawn.

Subsequently, a further inner sleeve 102 is rotated-in as far as possible through the inner sleeve 38. The inner sleeve has a distal end which can be inserted into the tool-holder 66. At the proximal side of the distal end, there is a short externally threaded section 104 which corresponds to the internal thread 26 so that the inner sleeve 102 can be screwed into the head 22.

In a next step, a multi-function sleeve is pushed over the clamping sleeve 36. The multi-function sleeve 106 comprises a connecting element coupling device 108, a spreading-device coupling device 110 as well as a holding instrument coupling device 112. The multi-function sleeve 106 has an internal wall surface 114 which is rotationally symmetrical with respect to the longitudinal axis 44. There are no projections protruding from the wall surface 114. Furthermore, there are also no projections protruding beyond the wall surface 114 in the direction of the longitudinal axis 44. Consequently, the multi-function sleeve can be rotated relative to the clamping sleeve 36 as long as the connecting element coupling device 108 and the connecting element 86 remain out of engagement. The internal wall surface 114 is circular in cross section and has a constant internal diameter parallel to the longitudinal axis 44. The multi-function sleeve 106 as a whole is thus symmetrical with respect to a plane 116 containing the longitudinal axis 44.

The connecting element coupling device 108 is arranged or formed at the distal end of the multi-function sleeve 106 such that it is coupled to the connecting element 86 in mutually non-rotational manner. This coupling between the multi-function sleeve 106 and the connecting element 86 is desired, in particular, when the connecting element 86 is already engaged in the first connecting element seating 28 of the bone screws 18, as is schematically illustrated in FIG. 7 for example. The connecting element coupling device 108 comprises at least one second connecting element seating 118 which is engageable with the connecting element 86 in force-and/or shape-locking manner. The second connecting element seating 118 comprises a recess 120 which, commencing from the distal end, is formed in a sleeve wall 122 of the multi-function sleeve and is open in the distal direction. It is thereby possible for the connecting element coupling device 108 to accommodate the connecting element 86, as is illustrated exemplarily in FIG. 8. The multi-function sleeve 106 thus serves, in particular, for holding down and positioning the connecting element 86 in the first connecting element seating 28 of the head 22.

In order to fix the position of the multi-function sleeve 106, there serves a knurled nut 124 which has an internal thread that corresponds to an external thread section 126 of the inner sleeve 102 which protrudes somewhat beyond a proximal end of the clamping sleeve 36 in the proximal direction when the inner sleeve 102 is inserted into the head 22 to the maximum extent. The multi-function sleeve 106 can thus be tightened against the connecting element 86 by screwing the knurled nut 124 in the distal direction. Due to this special construction, the multi-function sleeve 106 does not act directly on the head 22 or the head sleeve 24, but rather, only indirectly thereon via the connecting element 86.

If repositioning is necessary, i.e. changing the existing spacing between the vertebrae 14 in order to realign the spinal column 16 that has been compressed by the damaged vertebra 15, then one can optionally use a spreading device 128, namely when all the bone screws 18 are still coupled to the clamping sleeve 36 in the manner described way and whilst connected to the inner sleeve 102 and the multi-function sleeve 106, as is schematically illustrated in FIGS. 12 and 13. The spreading device 128 is formed in two-piece manner and comprises a lower spreader 130 and an upper spreader 132. Both the lower spreader and the upper spreader each comprise two coupling studs 134 and 136 which can be connected temporarily to the spreading-device coupling device 110. In order to enable interlocking engagement with the coupling studs 134 and 136 to be effected, the spreading-device coupling device 110 of each multi-function sleeve 106 comprises two coupling seatings 138 and 140, namely, the lower coupling seating 140 in the region of the distal end of the multi-function sleeve 106 and the upper coupling seating 138 which are both arranged or formed on an outer surface of the multi-function sleeve 106. Both coupling seatings 138 and 140 comprise a respective groove 142 and 144 which extends in parallel with the longitudinal axis 44 and is laterally undercut transverse to the longitudinal axis 44 on both sides. In addition, both coupling seatings 138 and 140 are open in the direction of the proximal end of the multi-function sleeve 106 for the introduction of the coupling studs 134 and 136 of the spreading device 128. The coupling studs 134 and 136 are rotationally symmetrical and have a T-shaped longitudinal section so that they can be pushed into the respective coupling seatings 138 and 140 from the proximal end in interlocking manner.

The lower spreader 130 is pushed into the lower coupling seatings 140 of two multi-function sleeves 106 with the two coupling studs 134. The coupling studs 136 of the upper spreader 132 are slid into the upper coupling seatings 138. Both spreaders 130 and 132 comprise respective spindle drives 146 and 148 with which the coupling studs 134 and 136 of the two mutually coupled multi-function sleeves 106 can be moved relative to each other. The spacing of the bone screws 18 can be adjusted by the lower spreader 130. The angle of inclination of the two coupled multi-function sleeves 106 can be adjusted by the upper spreader 132, thereby simultaneously enabling an inclination of the bone screws 18 and hence of the vertebrae 14 connected thereto in order to enable an inclination of the vertebrae 14 relative to each other to be adjusted. After repositioning has been effected, the individual steps of which are illustrated schematically in FIGS. 14 to 24, i.e. when the bone screws and hence the vertebrae 14 connected thereto are positioned in the desired way, each locking screw 96 just needs to be tightened for completing the process of implanting the spinal column stabilization system 12. To this end, the knurled nut is rotated back at least a quarter of a turn in the proximal direction so that the screw-driving tool 150 which is formed at the distal end of the inner sleeve 102 and corresponds to a tool-holder 152 of the locking screw 96 can engage in the tool-holder 152. A proximal end of the inner sleeve 102 can then be coupled to a handle 154 and the locking screw 96 tightened by hand.

In a next step, as is illustrated schematically in FIG. 9, the multi-function sleeve 106 can be coupled to a holding instrument 156 which has a fork-like end 158 that can be brought into engagement with the holding instrument coupling device 112 in shape-locking manner.

The holding instrument coupling device 112 is arranged or formed at the proximal end of the multi-function sleeve 106 for connecting it to the holding instrument 156 in mutually non-rotational releasable manner. The holding instrument coupling device 112 comprises a polyhedron 160 which may be in the form of an octagon 162 for example as illustrated in the Figures. This polyhedron 160 forms an end section 164 of the multi-function sleeve 106 defining the proximal end. The polyhedron 160 defines flat outer surface surfaces 166 which each incorporate a holding recess 168 facing away from the longitudinal axis 44. The holding recesses 168 are formed in the sleeve wall 122 of the multi-function sleeve 106 in the form of a through hole 170. The through hole 170 as a whole can be realized in the form of a boring 172. Furthermore, the multi-function sleeve 106 has a polyhedral stop 174 which adjoins the polyhedron 160 on the distal side and comprises a polyhedral stop surface 176 facing in the proximal direction. It should be noted furthermore, that the holding recesses 168 are arranged or formed closer to the polyhedral stop 174 than to the proximal end the multi-function sleeve 106.

The holding recesses 168 serve for seating corresponding projections which are arranged or formed on the forklike end 158 of the holding instrument 156. These can, in particular, be in the form of ball thrust pieces in order to enable defined coupling of the holding instrument 156 to the holding instrument coupling device 112 of the multi-function sleeve 106. The polyhedral stop 174 additionally prevents the holding instrument 156 from slipping off the polyhedron 160 in the distal direction.

In order to be able to tighten the locking screw 96 in a defined manner, the inner sleeve 102 is firstly unscrewed and a torque wrench 178 is inserted through the clamping sleeve 36. The holding instrument 156 serves for applying a counter-torque in order to prevent unwanted twisting of the spinal column stabilization system 12 that has been positioned in a defined way. The tightening torque applied to the locking screw 96 is thus introduced directly by the torque wrench 178. The counter-holding torque is introduced indirectly into the head 22 by the holding instrument 156 and the multi-function sleeve 106 via the connecting element 86.

Once the locking screw 96 has been tightened with the desired torque, the torque wrench 178 is pulled out in the proximal direction, the multi-function sleeve 106 is then withdrawn and the clamping sleeve 36 is subsequently removed.

Finally, the ends of the head sleeve 24 that are still present at the proximal side of the groove 32 can be gripped with pliers and broken off in order to ensure that the structure of the spinal column stabilization system 12 is as small as possible.

The apparatus 10 simplifies the surgical procedure since the multi-function sleeve 106 enables the clamping sleeve 36 to remain on the bone screw 18 and, at the same time, it can fulfil up to three functions, namely, the processes of holding the connecting element 86 down in the first connecting element seating 28 of the head sleeve 24, coupling to the spreading device 128 and also coupling to the holding instrument 156 for the purposes of introducing a counter-holding torque of the locking screw 96 by means of the torque wrench 178. A complicated dismantling of the clamping sleeve 36 can thereby be avoided, whereby fewer parts of the apparatus 10 have to be changed during the procedure. In addition, the indirect introduction of the counter-holding torque into the connecting element 86 via the holding instrument 156 and the multi-function sleeve 106 and not directly into the head 22 has the immediate advantage that smaller holding forces are sufficient for preventing an unwanted change in the position of the bone screw 18 when finally tightening the locking screw.

What is claimed:

1. A surgical apparatus for the implantation of a spinal column stabilization system, which spinal column stabilization system comprises at least two bone screws which are respectively anchorable in a vertebra of a spinal column and which respectively comprise at least one first connecting element seating, and at least one connecting element which corresponds to the first connecting element seating and is insertable and fixable therein, wherein the apparatus comprises at least one multi-function sleeve having a proximal and a distal end, which multi-function sleeve defines a longitudinal axis and comprises a connecting element coupling device, a spreading-device coupling device and a holding instrument coupling device, wherein the multi-function sleeve comprises an internal wall surface which is rotationally symmetrical with respect to the longitudinal axis, and wherein no projections protrude from the internal wall surface or beyond it in the direction of the longitudinal axis.

2. A surgical apparatus in accordance with claim 1, wherein the internal wall surface is circular in cross section and has a constant internal diameter parallel to the longitudinal axis.

3. A surgical apparatus in accordance with claim 1, wherein the multi-function sleeve is formed such as to be symmetrical with respect to a plane containing the longitudinal axis.

4. A surgical apparatus in accordance with claim 1, wherein the connecting element coupling device is arranged or formed at the distal end of the multi-function sleeve such as to couple to the connecting element in mutually non-rotational manner especially when the connecting element engages in the first connecting element seating of two bone screws.

5. A surgical apparatus in accordance with claim 1, wherein the connecting element coupling device comprises at least one second connecting element seating which is configured such as to be brought into engagement with the at least one connecting element in at least one of force- and shape-locking manner.

6. A surgical apparatus in accordance with claim 5, wherein the at least one second connecting element seating comprises a recess which, commencing from the distal end, is formed in a sleeve wall of the multi-function sleeve and is open in the distal direction.

7. A surgical apparatus in accordance with claim 1, wherein the spreading-device coupling device is configured for releasable connection to a spreading device for moving the two bone screws relative to each other, in particular, in a direction away from each other.

8. A surgical apparatus in accordance with claim 1, wherein the spreading-device coupling device comprises at least one coupling seating which is arranged on an outer surface of the multi-function sleeve.

9. A surgical apparatus in accordance with claim 8, wherein the at least one coupling seating comprises a groove which extends in parallel with a longitudinal axis defined by the multi-function sleeve and which, in particular, is undercut laterally transverse to the longitudinal axis on both sides.

10. A surgical apparatus in accordance with claim 8, wherein the at least one coupling seating is open in the direction of the proximal end for the insertion of a coupling stud of the spreading device.

11. A surgical apparatus in accordance with claim 8, characterized by two coupling seatings, wherein the one coupling seating is arranged or formed in the region of the distal end and wherein the other coupling seating is arranged or formed in the region of the proximal end.

12. A surgical apparatus in accordance with claim 1, wherein the spreading-device coupling device comprises at least one stop acting in the proximal direction.

13. A surgical apparatus in accordance with claim 12, wherein the at least one stop comprises a projection which is arranged on an outer surface of the multi-function sleeve and has at least one stop surface facing in the proximal direction.

14. A surgical apparatus in accordance with claim 1, wherein the holding instrument coupling device is arranged or formed at the proximal end for the purposes of connection to a holding instrument in releasable mutually non-rotational manner.

15. A surgical apparatus in accordance with claim 1, wherein the holding instrument coupling device comprises a polyhedron, in particular, an octagon which forms an end section of the multi-function sleeve defining the proximal end.

16. A surgical apparatus in accordance with claim 15, wherein the polyhedron defines flat outer surfaces and wherein at least one of the outer surfaces incorporates a holding recess facing away from the longitudinal axis.

17. A surgical apparatus in accordance with claim 16, wherein the holding recess is in the form of a through opening passing through a sleeve wall of the multi-function sleeve, in particular, in the form of a boring.

18. A surgical apparatus in accordance with claim 15, wherein the multi-function sleeve has a polyhedral stop which adjoins the polyhedron on the distal side and comprises at least one polyhedral stop surface facing in the proximal direction.

19. A surgical apparatus in accordance with claim 18, wherein the holding recess is arranged or formed closer to the polyhedral stop than to the proximal end of the multi-function sleeve.

20. A surgical apparatus in accordance with claim 1, wherein the multi-function sleeve is formed in one piece manner.

21. A surgical apparatus in accordance with claim 1, characterized by at least one clamping sleeve for producing a clamped connection, especially at a distal end thereof, to a head of one of the bone screws.

22. A surgical apparatus in accordance with claim 21, wherein the exterior of the clamping sleeve is dimensioned in such a manner that it is insertable at least partially, especially entirely, into the multi-function sleeve and is rotatable about the longitudinal axis relative thereto.

23. A surgical apparatus in accordance with claim 21, wherein the clamping sleeve comprises an outer sleeve and an inner sleeve that is insertable into the outer sleeve and in particular, wherein the outer sleeve is insertable into the multi-function sleeve.

24. A surgical apparatus in accordance with claim 1, characterized by at least one K-wire target device, a tissue protective sleeve, a dilation sleeve, a pedicle awl, a thread cutter for cutting a thread in a sclerotic bone and/or a screw length measuring instrument.

25. A surgical apparatus in accordance with claim 24, wherein the K-wire target device is insertable into the dilation sleeve and/or wherein the dilation sleeve is insertable into the tissue protective sleeve.

* * * * *